United States Patent
Seward

(10) Patent No.: US 10,441,747 B2
(45) Date of Patent: Oct. 15, 2019

(54) METHODS AND SYSTEMS FOR INHIBITING VASCULAR INFLAMMATION

(71) Applicant: Mercator MedSystems, Inc., Emeryville, CA (US)

(72) Inventor: Kirk Patrick Seward, San Francisco, CA (US)

(73) Assignee: Mercator MedSystems, Inc., San Leandro, CA (US)

( * ) Notice: Subject to any disclaimer, the term of this patent is extended or adjusted under 35 U.S.C. 154(b) by 218 days.

(21) Appl. No.: 14/605,865

(22) Filed: Jan. 26, 2015

(65) Prior Publication Data

US 2015/0141959 A1 May 21, 2015

Related U.S. Application Data

(63) Continuation-in-part of application No. 14/203,942, filed on Mar. 11, 2014, now Pat. No. 9,061,098, (Continued)

(51) Int. Cl.
*A61M 25/00* (2006.01)
*A61M 37/00* (2006.01)
(Continued)

(52) U.S. Cl.
CPC ............ *A61M 25/0084* (2013.01); *A61B 5/01* (2013.01); *A61B 5/021* (2013.01); *A61B 5/053* (2013.01);
(Continued)

(58) Field of Classification Search
CPC .. A61M 2025/0087; A61M 2025/0092; A61M 25/0084; A61M 2025/0057;
(Continued)

(56) References Cited

U.S. PATENT DOCUMENTS

| 5,112,305 A | 5/1992 | Barath et al. |
| 5,196,024 A | 3/1993 | Barath |

(Continued)

FOREIGN PATENT DOCUMENTS

| WO | WO 01/21157 A2 | 3/2001 |
| WO | WO-0121157 A2 | 3/2001 |

(Continued)

OTHER PUBLICATIONS

Christopher D. Owens MD, MSc et al, Safety and feasibility of adjunctive dexamethasone infusion into the adventitia of the femoropopliteal artery following endovascular revascularization, Available online Jan. 11, 2014, https://www.sciencedirect.com/science/article/pii/S0741521413018880?via%3Dihub. (Year: 2014).*

(Continued)

*Primary Examiner* — Shefali D Patel

(74) *Attorney, Agent, or Firm* — Wilson Sonsini Goodrich & Rosati

(57) ABSTRACT

Methods and kits for delivering pharmaceutical agents to an adventitia and other regions outside an external elastic lamina (EEL) surrounding a blood vessel utilize a catheter having a needle. The needle is positioned in up to 5 mm beyond the EEL and delivers an amount of a pharmaceutical agent sufficient to circumferentially permeate around the blood vessel and, in many cases, extend longitudinally and radially along the blood vessel. Confirmation that a delivery aperture of the needle lies beyond the EEL may be required before delivering the pharmaceutical agent. In one example, catheters are used to deliver dexamethasone and other anti-inflammatory agents to a peripheral vasculature and other vasculature to treat peripheral vascular disease and other conditions.

33 Claims, 17 Drawing Sheets

Related U.S. Application Data which is a continuation of application No. 12/790,541, filed on May 28, 2010, now Pat. No. 8,708,995, which is a continuation of application No. 10/691,119, filed on Oct. 21, 2003, now Pat. No. 7,744,584, which is a continuation-in-part of application No. 10/350,314, filed on Jan. 22, 2002.

(60) Provisional application No. 60/430,993, filed on Dec. 3, 2002, provisional application No. 60/370,602, filed on Apr. 5, 2002, provisional application No. 60/356,670, filed on Feb. 13, 2002, provisional application No. 60/350,564, filed on Jan. 22, 2002.

(51) Int. Cl.
| | | |
|---|---|---|
| *A61M 25/10* | (2013.01) | |
| *A61L 29/16* | (2006.01) | |
| *A61L 31/16* | (2006.01) | |
| *A61M 5/158* | (2006.01) | |
| *A61B 5/01* | (2006.01) | |
| *A61B 5/021* | (2006.01) | |
| *A61B 5/053* | (2006.01) | |
| *A61B 5/145* | (2006.01) | |
| *A61B 5/00* | (2006.01) | |

(52) U.S. Cl.
CPC ......... *A61B 5/14539* (2013.01); *A61B 5/4833* (2013.01); *A61L 29/16* (2013.01); *A61L 31/16* (2013.01); *A61L 2300/252* (2013.01); *A61L 2300/41* (2013.01); *A61L 2300/43* (2013.01); *A61M 5/158* (2013.01); *A61M 25/0043* (2013.01); *A61M 25/10* (2013.01); *A61M 37/0015* (2013.01); *A61M 2005/1588* (2013.01); *A61M 2025/0057* (2013.01); *A61M 2025/0087* (2013.01); *A61M 2025/0092* (2013.01); *A61M 2025/0093* (2013.01); *A61M 2025/0096* (2013.01); *A61M 2025/1086* (2013.01); *A61M 2210/12* (2013.01)

(58) Field of Classification Search
CPC ...... A61M 2025/0096; A61M 2210/12; A61M 25/0082; A61M 25/0087; A61M 25/0092; A61L 2300/43; A61L 2300/41
See application file for complete search history.

(56) References Cited

U.S. PATENT DOCUMENTS

| | | |
|---|---|---|
| 5,270,047 A | 12/1993 | Kauffman et al. |
| 5,354,279 A | 10/1994 | Hofling |
| 5,527,532 A | 6/1996 | Edelman et al. |
| 5,538,504 A | 7/1996 | Linden et al. |
| 5,645,564 A | 7/1997 | Northrup et al. |
| 5,681,281 A | 10/1997 | Vigil et al. |
| 5,693,029 A | 12/1997 | Leonhardt |
| 5,722,989 A | 3/1998 | Fitch et al. |
| 5,866,561 A | 2/1999 | Ungs |
| 5,900,246 A * | 5/1999 | Lambert ............. A61L 27/34 424/427 |
| 6,009,877 A | 1/2000 | Edwards |
| 6,059,815 A | 5/2000 | Lee et al. |
| 6,102,933 A | 8/2000 | Lee et al. |
| 6,210,392 B1 | 4/2001 | Vigil et al. |
| 6,302,870 B1 | 10/2001 | Jacobsen et al. |
| 6,283,947 B1 | 11/2001 | Mirzaee |
| 6,334,856 B1 | 1/2002 | Allen et al. |
| 6,494,862 B1 * | 12/2002 | Ray ................. A61M 25/0084 604/103.01 |
| 6,547,303 B1 | 4/2003 | Anderson |
| 6,547,803 B2 | 4/2003 | Seward et al. |
| 6,625,486 B2 | 9/2003 | Lundkvist et al. |
| 6,860,867 B2 | 3/2005 | Seward et al. |
| 7,008,411 B1 * | 3/2006 | Mandrusov ....... A61M 25/1006 604/164.01 |
| 7,094,765 B1 | 8/2006 | Iversen et al. |
| 7,247,149 B2 | 7/2007 | Beyerlein |
| 9,884,013 B2 | 2/2018 | Seward et al. |
| 2002/0001581 A1 | 1/2002 | Lynch et al. |
| 2002/0052404 A1 * | 5/2002 | Hunter ................. A61K 9/0024 514/449 |
| 2002/0188310 A1 | 12/2002 | Seward et al. |
| 2003/0040712 A1 | 2/2003 | Ray et al. |
| 2003/0078562 A1 | 4/2003 | Makower et al. |
| 2003/0120297 A1 | 6/2003 | Beyerlein |
| 2003/0170287 A1 * | 9/2003 | Prescott ............... A61K 9/0024 424/423 |
| 2003/0171734 A1 | 9/2003 | Seward et al. |
| 2004/0067197 A1 | 4/2004 | Leclerc et al. |
| 2004/0138643 A1 | 7/2004 | Seward et al. |
| 2004/0162542 A1 | 8/2004 | Wilber et al. |
| 2004/0260240 A1 | 12/2004 | Beyerlein |
| 2004/0260268 A1 * | 12/2004 | Falotico ................. A61F 2/91 604/500 |
| 2005/0090714 A1 | 4/2005 | Greff |
| 2005/0158361 A1 | 7/2005 | Dhondt et al. |
| 2005/0182071 A1 | 8/2005 | Seward et al. |
| 2005/0232965 A1 | 10/2005 | Falotico |
| 2006/0069349 A1 | 3/2006 | Ganz et al. |
| 2006/0115903 A1 * | 6/2006 | Ridker ............... G01N 33/6863 436/71 |
| 2006/0122684 A1 | 6/2006 | Lye et al. |
| 2006/0189941 A1 | 8/2006 | Seward et al. |
| 2007/0078620 A1 | 4/2007 | Seward et al. |
| 2007/0100318 A1 | 5/2007 | Seward et al. |
| 2007/0100319 A1 | 5/2007 | Seward et al. |
| 2007/0100320 A1 | 5/2007 | Seward et al. |
| 2007/0106248 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106252 A1 | 5/2007 | Seward et al. |
| 2007/0106253 A1 | 5/2007 | Seward et al. |
| 2007/0106254 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0129789 A1 | 6/2007 | Cottone et al. |
| 2007/0269385 A1 | 11/2007 | Yun et al. |
| 2008/0038316 A1 | 2/2008 | Wong et al. |
| 2009/0204104 A1 * | 8/2009 | Tremble ............. A61M 25/0084 604/509 |
| 2010/0082095 A1 | 4/2010 | Pacetti et al. |
| 2010/0305546 A1 | 12/2010 | Seward et al. |
| 2013/0029950 A1 | 1/2013 | Bischoff et al. |
| 2013/0035665 A1 * | 2/2013 | Chu ....................... A61L 31/14 604/509 |
| 2013/0224255 A1 | 8/2013 | Hossainy et al. |
| 2014/0296279 A1 | 10/2014 | Seward et al. |
| 2014/0303569 A1 | 10/2014 | Seward et al. |
| 2018/0169075 A1 | 6/2018 | Kirk |

FOREIGN PATENT DOCUMENTS

| | | |
|---|---|---|
| WO | WO-2010104584 A2 | 9/2010 |
| WO | WO-2014118696 A2 | 8/2014 |
| WO | WO-2017078405 A1 | 5/2017 |

OTHER PUBLICATIONS

International search report and written opinion dated Mar. 17, 2016 for PCT/US2016/014819.

Notice of allowance dated Apr. 23, 2015 for U.S. Appl. No. 14/203,942.

U.S. Appl. No. 09/961,079, filed Sep. 20, 2001, Seward, et al.

Altman et al., Exploring heart lymphatics in local drug delivery, Lymph. Res. Biol., (2003) 1:47-54.

(56) References Cited

OTHER PUBLICATIONS

Barath et al., "Infiltrator Angioplasty Balloon Catheter: a device for combined angioplasty and intramural site-specific treatment," Cathet Cardiovasc Diagn. Jul. 1997;41(3):333-341.

Chandrasekar et al., "Coronary Artery Endothelial. Protection After Local Delivery of 17 $\beta$-Estradiol During Balloon Angioplasty in a Porcine Model : A Potential New Pharmacologic Approach to Improve Endothelial Function," J. Am. Col. Cardiol. (2001), 38(5):1570-1576.

Chandrasekar et al., "Local Delivery of 17-Beta-Estradiol Decreases Neointimal Hyperplasia After Coronary Angioplasty in a Porcine Model," J. Am. Col. Cardiol. (2000), 36(6):1972-1978.

Creel, "Arterial Paclitaxel Distribution and Deposition," Circulation Research. Apr. 2000;86:879-884.

Dai-Do et al., "17 beta-estradiol inhibits proliferation and migration of human vascular smooth muscle cells: similar effects in cells from postmenopausal females and in males," Cardiovasc Res. Nov. 1996;32(5):980-985.

Daschner et al., Penetration of gentamicin into heart valves, subcutaneous and muscular tissue of patients undergoing open heart surgery, J. Cardiovasc. Surg., (1986) 581-584.

Laham et al., Intracoronary and intravenous administration of basic fibroblast growth factor: myocardial and tissue distribution, Drug Met. Disp., (1999) 27:821-826.

Laham et al., Intrapericardial administration of basic fibroblast growth factor: myocardial and tissue distribution and comparison with intracoronary and intravenous administration, Cath Cardio. Interv., (2003) 58:375-381.

Nikol et al., "Needle Injection Catheter Delivery of the Gene for an Antibacterial Agent Inhibits Neointimal Formation," Gene Therapy, May 1999, vol. 6, No. 5, pp. 737-748.

Notice of allowance dated Feb. 23, 2010 for U.S. Appl. No. 10/691,119.
Notice of allowance dated Dec. 26, 2013 for U.S. Appl. No. 12/790,541.
Office action dated Jan. 30, 2007 for U.S. Appl. No. 10/350,314.
Office action dated Feb. 2, 2011 for U.S. Appl. No. 12/790,541.
Office action dated Feb. 26, 2009 for U.S. Appl. No. 10/691,119.
Office action dated Apr. 16, 2008 for U.S. Appl. No. 10/691,119.
Office action dated May 15, 2008 for U.S. Appl. No. 10/350,314.
Office action dated May 16, 2007 for U.S. Appl. No. 10/350,314.
Office action dated Jun. 25, 2007 for U.S. Appl. No. 11/601,290.
Office action dated Jun. 25, 2007 for U.S. Appl. No. 11/607,177.
Office action dated Jun. 27, 2007 for U.S. Appl. No. 11/607,168.
Office action dated Jun. 27, 2007 for U.S. Appl. No. 11/607,170.
Office action dated Jun. 27, 2007 for U.S. Appl. No. 11/607,172.
Office action dated Jun. 27, 2007 for U.S. Appl. No. 11/607,175.
Office action dated Jun. 27, 2007 for U.S. Appl. No. 11/607,176.
Office action dated Jun. 27, 2007 for U.S. Appl. No. 11/607,356.
Office action dated Jul. 2, 2007 for U.S. Appl. No. 11/607,355.
Office action dated Jul. 14, 2006 for U.S. Appl. No. 10/350,314.
Office action dated Jul. 16, 2007 for U.S. Appl. No. 11/607,166.
Office action dated Jul. 16, 2007 for U.S. Appl. No. 11/607,167.
Office action dated Jul. 16, 2007 for U.S. Appl. No. 11/607,178.
Office action dated Jul. 16, 2007 for U.S. Appl. No. 11/607,658.
Office action dated Jul. 17, 2007 for U.S. Appl. No. 11/607,169.
Office action dated Aug. 20, 2008 for U.S. Appl. No. 10/350,314.
Office action dated Aug. 20, 2008 for U.S. Appl. No. 10/691,119.
Office action dated Aug. 24, 2007 for U.S. Appl. No. 10/350,314.
Office action dated Sep. 15, 2009 for U.S. Appl. No. 10/691,119.
Office action dated Oct. 11, 2011 for U.S. Appl. No. 12/790,541.
Office action dated Dec. 12, 2006 for U.S. Appl. No. 10/691,119.

Pharmacia & Upjohn Company, "Depo-Estradiol," Product/Prescription Information [pamphlet], (Aug. 2000), 6 pages total.

Solmon et al., "Amiodarone versus a [3-blocker to prevent atrial fibrillation after cardiovascular surgery," AHJ, Nov. 2001; 142(5):811-815.

ClinicalTrials.gov. Identifier: NCT01507558. Dexamethasone Infusion to the Adventitia to Enhance Clinical Efficacy After Femoropopliteal Revascularization (DANCE). https://clinicaltrials.gov/ct2/show/NCT01507558?term=nct01507558&rank=1. Last updated Aug. 15, 2014. Accessed on Mar. 4, 2015. 4 pages.

Gaspardone, et al. C-Reactive protein, clinical outcome, and restenosis rates after implantation of different drug-eluting stents. Am J Cardiol. May 1, 2006;97(9):1311-6. Epub Mar. 20, 2006.

Han, et al. The favorable clinical and angiographic outcomes of a high-dose dexamethasone-eluting stent: randomized controlled prospective study. Am Heart J. Nov. 2006;152(5):887.e1-7.

Konig, et al. Randomized comparison of dexamethasone-eluting stents with bare metal stent implantation in patients with acute coronary syndrome: serial angiographic and sonographic analysis. Am Heart J. Jun. 2007;153(6):979.e1-8.

Office action dated Jan. 9, 2015 for U.S. Appl. No. 14/203,942.

Schillinger, et al. Balloon angioplasty and stent implantation induce a vascular inflammatory reaction. J Endovasc Ther. Feb. 2002;9(1):59-66.

Ayers et al., "Amiodarone instilled into the canine pericardial sac migrates transmurally to produce electrophysiologic effects and suppress atrial fibrillation," Journal of Cardiovascular Electrophysiology, 7(8): 713-21 (Aug. 1996).

Ikeno et al., "Novel percutaneous adventitial drug delivery system for regional vascular treatment, " Catheter Cardiovasc. interv., (2004) 63: 220-230.

International search report dated Apr. 21, 2004 for PCT/US03/02130.

Co-pending U.S. Appl. No. 16/058,690, filed Aug. 8, 2018.

Owens, Christopher D. et al. Safety and feasibility of adjunctive dexamethasone infusion into the adventitia of the femoropopliteal artery following endovascular revascularization. Journal of Vascular Surgery 59(4):1016-1024 (Apr. 2014).

Owens, Christopher D., MD. Pilot Results from Dance: Dexamethasone to the Adventitia to Enhance Clinical Efficacy in PAD. pp. 1-19 (2012).

Bruun JM et al., Monocyte chemoattractant protein-1 release is higher in visceral than subcutaneous human adipose tissue (AT): implication of macrophages resident in the AT. J Clin Endocrinol Metab 2005;90:2282-9.

Franchimont D. et al., Tumor necrosis factor alpha decreases, and interleukin-10 increases, the sensitivity of human monocytes to dexamethasone: potential regulation of the glucocorticoid receptor. J Clin Endocrinol Metab 1999;84:2834-9.

Wildgruber M, et al. Early endothelial and haematological response to cryoplasty compared with balloon angioplasty of the superficial femoral artery—a pilot study. British Journal of Radiology 2007;80:430-436.

Heider P, et al. Role of adhesion molecules in the induction of restenosis after angioplasty in the lower limb. J Vas Surg 2006;43:969-77.

Cipollone F, et al. Elevated Circulating Levels of Monocyte Chemoattractant Protein-1 in Patients With Restenosis After Coronary Angioplasty. Arterioscler Thromb Vasc Biol 2001;21:327-334.

Ross R, Glomset JA. The pathogenesis of atherosclerosis (first of two parts). N Engl J Med. 1976;295:369-377.

Ross R, Glomset JA. The pathogenesis of atherosclerosis (second of two parts). N Engl J Med. 1976;295:420-425.

Libby P. Inflammation in Atherosclerosis. Arterioscler Thromb Vasc Biol. 2012;32:2045-2051.

Co-pending U.S. Appl. No. 15/990,167, filed May 25, 2018.

European Application No. 16743927.2-1109 Extended European Search Report dated Aug. 17, 2018.

Gasper, W. et al. Adventitial Nab-Rapamycin Injection Reduces Porcine Femoral Artery Luminal Stenosis Induced by Balloon Angioplasty via Inhibition of Medial Proliferation and Adventitial Inflammation. Circulation: Cardiovascular Interventions. 6(6):701-709 (Dec. 1, 2013).

International Application No. PCT/US17/52790 International Search Report and Written Opinion dated Dec. 8, 2017.

International Application No. PCT/US18/34713 International Search Report and Written Opinion dated Oct. 19, 2018.

International Application No. PCT/US18/34713 Search Report and Written Opinion dated Oct. 19, 2018.

(56) References Cited

OTHER PUBLICATIONS

Siablis, D. et al. Sirolimus-Eluting Versus Bare Stents After Suboptimal Ingrapopliteal Angioplastry for Critical Limb Ischemia: Enduring 1-Year Angiographic and Clinical Benefit, J. Endovasc. Ther. 14:241-250 (2007).
U.S. Appl. No. 15/890,857 Final Office Action dated Nov. 14, 2018.
U.S. Appl. No. 15/890,857 Non-Final Office Action dated May 30, 2018.

* cited by examiner

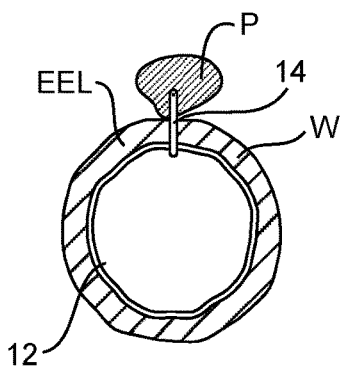 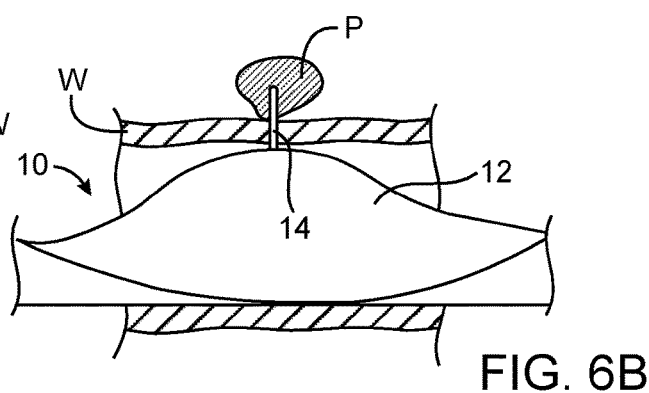
FIG. 6A  FIG. 6B
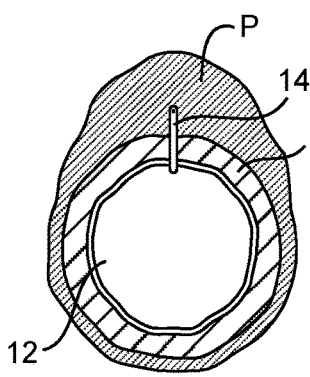 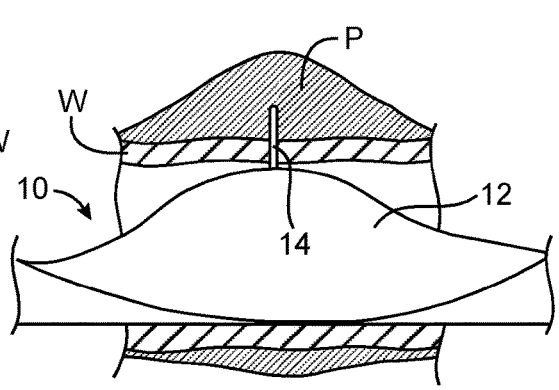
FIG. 7A  FIG. 7B
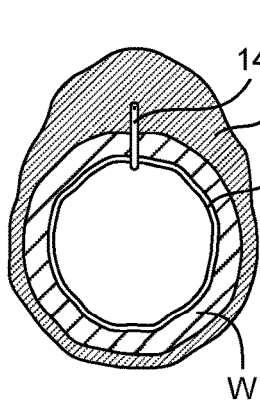 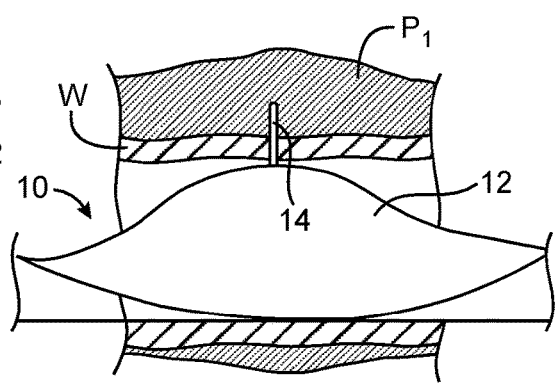
FIG. 8A  FIG. 8B 1.0 mL infusion at 9 cm 1.0 mL infusion at 13.5 cm 1.0 mL infusion at 17 cm NOTE: Cipollone examined MCP-1 in plasma after PTCA; DANCE in serum after peripheral PTA

METHODS AND SYSTEMS FOR INHIBITING VASCULAR INFLAMMATION

CROSS-REFERENCE TO RELATED APPLICATIONS

This application is a continuation-in-part of U.S. patent application Ser. No. 14/203,942, filed on Mar. 11, 2014, which is a continuation of U.S. patent application Ser. No. 12/790,541, filed on May 28, 2010, which is a continuation of U.S. patent application Ser. No. 10/691,119, filed on Oct. 21, 2003, which is a continuation-in-part of U.S. patent application Ser. No. 10/350,314, filed on Jan. 22, 2003, which claimed the benefit of each of the following U.S. Provisional Patent Applications, No. 60/350,564, filed Jan. 22, 2002; 60/356,670, filed Feb. 13, 2002; 60/370,602, filed Apr. 5, 2002; and 60/430,993, filed Dec. 3, 2002; the full disclosures of each of these prior provisional and non-provisional applications are incorporated herein by reference.

BACKGROUND OF THE INVENTION

1. Field of the Invention

The present invention relates generally to medical methods and devices. More particularly, the present invention relates to medical methods and kits for distributing pharmaceutical agents in the adventitial tissue surrounding a blood vessel.

Coronary artery disease is the leading cause of death and morbidity in the United States and other western societies. In particular, atherosclerosis in the coronary arteries can cause myocardial infarction, commonly referred to as a heart attack, which can be immediately fatal or, even if survived, can cause damage to the heart which can incapacitate the patient. Other coronary diseases which cause death and incapacitation include congestive heart failure, vulnerable or unstable plaque, and cardiac arrhythmias. In addition to coronary artery disease, diseases of the peripheral vasculature can also be fatal or incapacitating. Blood clots and thrombus may occlude peripheral blood flow, leading to tissue and organ necrosis. Deep vein thrombosis in the legs can, in the worse cases, requiring amputation. Clots in the carotid artery can embolize and travel to the brain, potentially causing ischemic stroke.

While coronary artery bypass surgery is an effective treatment for stenosed arteries resulting from atherosclerosis and other causes, it is a highly invasive procedure which is also expensive and which requires substantial hospital and recovery time. Percutaneous transluminal coronary angioplasty (PTCA), commonly referred to as balloon angioplasty, is less invasive, less traumatic, and significantly less expensive than bypass surgery. Until recently, however, balloon angioplasty has not been considered to be as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in reducing subsequent restenosis resulting from hyperplasia.

Despite such improvement, patients who have undergone angioplasty procedures with subsequent stenting still suffer from a high incidence of restenosis resulting from hyperplasia. Very recently, however, experimental trials have demonstrated that the implanting of stents which have been coated with anti-proliferative drugs can significantly reduce the occurrence of hyperplasia, promising to make combined angioplasty and stenting a viable alternative to bypass surgery.

As an alternative to stent-based luminal drug delivery, the direct delivery of drug into vascular and other luminal walls has been proposed. For some time, the use of intravascular catheters having porous balloons, spaced-apart isolation balloons, expandable sleeves, and the like, have been used for releasing drugs into the inner surface of the endothelial wall of blood vessels.

Congestive heart failure and cardiac arrhythmias, although sometimes related to coronary artery disease, are usually treated differently than are occlusive diseases. Congestive heart failure is most often treated pharmaceutically, although no particular drug regimens have proven to be highly effective. Proposed mechanical approaches for treating congestive heart failure include constraints for inhibiting further dilation of the heart muscle, and pace makers and mechanical devices for enhancing heart function. Cardiac arrhythmias may also be treated with drug therapies, and reasonably effective intravascular treatments for ablating aberrant conductive paths on the endocardial surfaces also exist. No one treatment, however, for either of these conditions is completely effective in all cases.

Of particular interest to the present invention, catheters carrying microneedles capable of delivering therapeutic and other agents deep into the adventitial layer surrounding blood vessel lumens have been described in U.S. Pat. No. 6,547,303, and co-pending application Ser. No. 09/961,079, filed on Sep. 20, 2001, both having common inventorship with but different assignment than the present application, the full disclosures of which are incorporated herein by reference.

Pharmaceutical therapies for coronary artery and other cardiac and vascular diseases can be problematic in a number of respects. First, it can be difficult to achieve therapeutically effective levels of a pharmaceutical agent in the cardiac tissues of interest. This is particularly true of systemic drug delivery, but also true of various intravascular drug delivery protocols which have been suggested. The release of a pharmaceutical agent directly on to the surface of a blood vessel wall within the heart or the peripheral vasculature frequently results in much or most of the drug being lost into the luminal blood flow. Thus, drugs which are difficult to deliver across the blood vessel wall will often not be able to reach therapeutically effective concentrations in the targeted tissue. Second, even when drugs are successfully delivered into the blood vessel wall, they will frequently lack persistence, i.e., the drug will be rapidly released back into the blood flow and lost from the targeted tissues. Third, it is frequently difficult to intravascularly deliver a pharmaceutical agent to remote and/or distributed diseased regions within a blood vessel. Most prior intravascular drug delivery systems, at best, deliver relatively low concentrations of the pharmaceutical agent into regions of the blood vessel wall which are directly in contact with the delivery catheter. Thus, diseased regions which may be remote from the delivery site(s) and/or which include multiple spaced-apart loci may receive little or no therapeutic benefit from the agent being delivered. In particular, most if not all prior intravascular drug delivery apparatus have been unable to deliver the drug over large volumetric regions of tissue, particularly in a manner which achieves relatively consistent drug concentrations. Fourth, delivery of a pharmaceutical agent into the blood vessel wall may be insufficient to treat the underlying cause of disease. For example, delivery of anti-proliferative agents into the blood vessel wall may have limited benefit in inhibiting the smooth muscle cell migration which is believed to be a cause of intimal hyperplasia or cell proliferation characteristic of neoplastic diseases. Fifth, the etiology of the vascular disease may itself inhibit effective delivery of a pharmaceutical agent. Thus, systems and protocols which are designed to deliver drug into blood vessel wall at the site of disease may be limited in their effectiveness by the nature of the disease itself.

For these reasons, it would be desirable to provide additional and improved methods and kits for the intravascular delivery of pharmaceutical agents to treat coronary cerebral, hepatic, peripheral, and other vascular diseases. Such additional and improved methods and kits would preferably also be adaptable to treat non-vascular diseases, including cancers and other neoplastic diseases, diseases associated with particular organs or other compartmentalized tissue regions, and other conditions which might benefit from remote localized delivery of drugs via the vasculature. In particular, it would be beneficial to provide methods which enhance the therapeutic concentrations of the pharmaceutical agents in diseased and other targeted tissues, not just the blood vessel walls. For example, it would be particularly desirable if the methods and systems could provide for an extended volumetric distribution of the delivered pharmaceutical agent including both longitudinal and radial spreading from the injection site(s) in order to provide therapeutic dosage levels of the agent within the heart, liver, or other organ or compartmentalized tissue region. It would be further beneficial if the methods could efficiently deliver the drugs into the targeted tissue and limit or avoid the loss of drugs into the luminal blood flow. Similarly, it would beneficial to enhance the therapeutic concentrations of the pharmaceutical agent delivered to a particular targeted tissue. It would be still further beneficial if the persistence of such therapeutic concentrations of the pharmaceutical agent in the tissue were also increased, particularly in targeted tissues away from the blood vessel wall, including the adventitial tissue surrounding the blood vessel wall. Additionally, it would be beneficial to increase the uniformity and extent of pharmaceutical agent delivery over remote, extended, and distributed regions of the adventitia and other tissues surrounding the blood vessels. In some instances, it would be beneficial to provide methods which permit the delivery of pharmaceutical agents through the blood vessel walls at non-diseased sites within the blood vessel, where the agent would then be able to migrate through the adventitia or other tissues to the diseased site(s). At least some of these objectives will be met by the inventions described hereinafter. Still further, it would be desirable if such intravascular delivery of pharmaceutical agents would be useful for treating diseases and conditions of the tissues and organs in addition to those directly related to the heart or vasculature.

2. Description of the Background Art

U.S. Pat. No. 6,547,803 B2, and published Application 2003/0171734A1 both having common inventorship with but different assignment than the present application, describe microneedle catheters which may be used in at least some of the methods described in the present application. Drug distribution through the collateral circulation in the heart is discussed in Daschner et al. (1986) J. Cardiovasc. Surg. 581-584; Laham et al. (1999) Drug Met. Disp. 27:821-826; Laham et al. (2003) Cath. Cardio. Interv. 58:375-381; and Altman et al. (2003) Lymph. Res. Biol. 1:47-54. Dexamethasone-eluting stents have been used to treat vascular disease as described in Gaspardone A, et al., Am J Cardiol 97:1311-1316 (2006); Han S H, et al., Am Heart J 152:887 (2006); and König A, et al., Am Heart J 153:979 (2007).

BRIEF SUMMARY OF THE INVENTION

Methods and kits according to the present invention are able to achieve enhanced concentrations of many pharmaceutical agents in targeted tissues surrounding a blood vessel, particularly adventitial tissues, more particularly coronary adventitial tissues. The methods rely on intravascular delivery of the pharmaceutical agent using a catheter having a deployable needle, usually a small needle or a microneedle. The catheter is advanced intravascularly to a target injection site (which may or may not be a diseased region) in a blood vessel. The needle is advanced through the blood vessel wall so that an aperture on the needle is positioned in a perivascular region (defined below) surrounding the injection site, and the pharmaceutical agent is delivered into the perivascular region through the microneedle.

In particular, the methods of the present invention are intended for a volumetric distribution of a pharmaceutical agent in the tissue of a living host. By "volumetric distribution," it is meant that the pharmaceutical agent will be able to distribute both longitudinally and radially with respect to the axis of the blood vessel from which the agent is being injected. Typically, the agent will be able to distribute over a distance of at least 1 cm longitudinally and at least 1 cm radially from the site of injection over a time period no greater than 60 minutes. Usually, the volumetric distribution will be significantly greater than that, and a concentration of the agent measured at all locations at least 2 cm from the delivery site will be at least 10% of the concentration at the delivery site, again preferably after a period of 60 minutes.

While the present invention does not depend upon an understanding of the distribution mechanism, for completeness, it is noted that the inventors herein believe that this volumetric distribution results from delivery of the pharmaceutical agent into the lymphatic micro circulatory system surrounding the blood vessel from which the agent is directed.

Regardless of the actual mechanism, the methods herein preferably rely on positioning an aperture of the needle within the target blood vessel so that the aperture lies beyond an external elastic lamina (EEL) of the blood vessel wall by a distance not exceeding 5 mm, usually not exceeding 3 mm, and preferably not exceeding 0.5 mm. The lower end of the range is less critical, and it is necessary only that the aperture be at least partly beyond the other periphery of the EEL. For lymphatic distribution, it is preferred to deliver pharmaceutical agents having dimensions which do not exceed 200 nm, as larger substances are not efficiently distributed by the lymphatic distribution system.

The methods, systems, and kits of the present invention will find particular use in the coronary vasculature, including the arterial and venous vasculature, for treating a variety of conditions, including post-angioplasty and post-stenting hyperplasia, cardiac failure, coronary revascularization, and the like. The present invention will, however, also find use outside of the coronary vasculature, including but not limited to use in the cerebral vasculature, the hepatic vasculature, the peripheral vasculature, and the vasculature of other organs and tissue compartments within a patient. The pharmaceutical agents may be delivered to treat virtually any condition which is amenable to localized drug delivery, including the delivery of anti-neoplastic agents to treat tumors and other neoplastic conditions, the delivery of antibiotics and other anti-infective agents to treat infections and other pathogen-based diseases, and the like.

This delivery protocol has been found to have a number of unexpected advantages. First, direct injection into the perivascular region has been found to immediately provide relatively high concentrations of the pharmaceutical agent in volume immediately surrounding the injected tissue. Second, following injection, it has been found that the injected agents will distribute circumferentially to substantially uniformly surround the blood vessel at the injection site as well as longitudinally to reach positions which are 1 cm, 2 cm, 5 cm, or more away from the injection site. In particular, the injected pharmaceutical agents have been found to distribute transmurally throughout the endothelial and intimal layers of the blood vessel, as well as in the media, or muscular layer, of the blood vessel wall. In the coronary arteries, in addition to circumferential and longitudinal migration, the pharmaceutical agent can migrate through the myocardium to reach the adventitia and wall structures surrounding blood vessels other than that through which the agent has been injected. Pathways for the distribution of the pharmaceutical agent are presently believed to exist through the pericardial space and the sub-epicardial space and may also exist in the vasa vasorum and other capillary channels through the muscle and connective tissues. Third, the delivered and distributed pharmaceutical agent(s) will persist for hours or days and will release back into the blood vessel wall over time. Thus, a prolonged therapeutic effect based on the pharmaceutical agent may be achieved in both the adventitia and the blood vessel wall. Fourth, after the distribution has occurred, the concentration of the pharmaceutical agent throughout its distribution region will be highly uniform. While the concentration of the pharmaceutical agent at the injection site will always remain the highest, concentrations at other locations in the peripheral adventitia around the injection site will usually reach at least about 10% of the concentration at the injection site, often being at least about 25%, and sometimes being at least about 50%. Similarly, concentrations in the adventitia at locations longitudinally separated from the injection site by about 5 cm will usually reach at least 5% of the concentration at the injection site, often being at least 10%, and sometimes being at least 25%. Finally, the methods of the present invention will allow for the injection of pharmaceutical agents through non-diseased regions of the coronary and peripheral vasculature to treat adjacent or remote diseased regions of the vasculature. The latter is of particular advantage since the diseased regions may be refractory to effective microneedle or other intravascular delivery protocols. Thus, pharmaceutical agent(s) can be delivered into the adventitia surrounding the diseased regions through remote injection sites.

The benefits of the present invention are achieved by delivering the pharmaceutical agents into a perivascular region surrounding a coronary artery or other blood vessel. The perivascular region is defined as the region beyond external elastic lamina of an artery or beyond the tunica media of a vein. Usually, injection will be made directly into the vasa vasorum region of the adventitia, and it has been found that the pharmaceutical agent disperses through the adventitia circumferentially, longitudinally, and transmurally from injection site. Such distribution can provide for delivery of therapeutically effective concentrations of many drugs which would be difficult to administer in other ways.

The adventitia is a layer of fatty tissue surrounding the arteries of the human and other vertebrate cardiovascular systems. The external elastic lamina (EEL) separates the fatty adventitial tissue from muscular tissue that forms the arterial wall. Microneedles of the present invention pass through the muscular tissue of the blood vessel and the EEL in order to reach the perivascular space into which the drug is injected. The drugs will typically either be in fluid form themselves, or will be suspended in aqueous or fluid carriers in order to permit dispersion of the pharmaceutical agents through the adventitia.

The adventitial tissue has a high concentration of lipids which will preferentially solubilize lipophilic pharmaceutical agents and hydrophilic or other pharmaceutical agents which are incorporated into lipophilic carriers, adjuvants, or the like. Both lipophilic and non-lipophilic pharmaceutical agents will have the ability to diffuse within and through the adventitia, with the rate and extent of such diffusion being controlled, at least in part, by the degree and nature of the lipophilic moieties present in the pharmaceutical agents. Thus, when pharmaceutical agents are injected, either by themselves or in an aqueous carrier, the agents may tend to be preferentially absorbed by the lipids in the adventitia. Pharmaceutical agents do not, however, remain localized at the site of injection, but instead will migrate and spread through the adventitia to locations remote from the injection site. The affinity between the pharmaceutical agents and the lipids in the adventitia, however, will provide for a controlled and sustained release of the lipophilic and other pharmaceutical agents over time. Thus, delivery of pharmaceutical agents into the adventitia creates a biological controlled release system for the agents. In particular, the pharmaceutical agents will slowly be released back from the adventitia into the muscle and other layers of the blood vessel wall to provide for prolonged pharmacological treatment of those areas. Such prolonged treatments can be particularly useful for inhibiting vascular hyperplasia and other conditions which are thought to initiate within the smooth muscle cells and other components of the blood vessel wall.

Pharmaceutical agents formulated to provide for sustained or controlled release of the pharmacologically active substances may be introduced directly into the adventitia by injection using the microneedle of the present invention. Numerous particular controlled release formulations are known in the art. Exemplary formulations include those which provide for diffusion through pores of a microcarrier or other particle, erosion of particles or barrier films, and combinations thereof. In addition, microparticles or nanoparticles of pure (neat) pharmaceutical substances may be provided. Cross-linked forms of such substances may also be utilized, and combinations thereof with erodable polymers may be employed. Other conventional formulations, such as liposomes, solubilizers (e.g. cyclodextrins), and the like, may be provided to control release of the active substance in the pharmaceutical agent.

In a first aspect of the present invention, a method for distributing a pharmaceutical agent in the adventitial tissue of a living vertebrate host's heart, such as a human heart, comprises positioning a microneedle through the wall of a coronary blood vessel and delivering an amount of the pharmaceutical agent therethrough. The aperture of the microneedle is located in a perivascular space surrounding the blood vessel, and the pharmaceutical agent distributes substantially completely circumferentially through adventitial tissue surrounding the blood vessel at the site of the microneedle. Usually, the agent will further distribute longitudinally along the blood vessel over a distance of at least 1 cm, often a distance of a least 5 cm, and sometimes a distance of at least 10 cm, within a time period no greater than 60 minutes, often within 5 minutes of less. While the concentration of the pharmaceutical agent in the adventitia will decrease in the longitudinal direction somewhat, usually, the concentration measured at a distance of 5 cm from the injection site will be at least 5% of the concentration measured at the same time at the injection site, often being at least 10%, frequently being as much as 25%, and sometimes being as much as 50%.

The aperture of the microneedle will be positioned so that it lies beyond the external elastic lamina (EEL) of the blood vessel wall and into the perivascular region surrounding the wall. Usually, the aperture will be positioned at a distance from the inner wall of the blood vessel which is equal to at least 10% of the mean luminal diameter of the blood vessel at the injection site. Preferably, the distance will be in the range from 10% to 75% of the mean luminal diameter. The amounts of the pharmaceutical agent delivered into the perivascular region may vary considerably, but will typically be in the range from 10 μl to 5000 μl, typically being from 100 μl to 1000 μl, and often being from 250 μl to 500 μl. Such methods for distributing pharmaceutical agents will be most often used in coronary arteries, typically for the treatment of hyperplasia or vulnerable plaque. The methods may further find use, however, in patients suffering from other vascular diseases, such as those in the peripheral vasculature, and in patients suffering from coronary conditions, including congestive heart failure, cardiac arrhythmias, and the like. In the latter cases, the methods of the present invention are particularly useful in delivering pharmaceutical agents widely and uniformly through the myocardium by using one or a relatively low number of injections in the coronary vasculature.

In a second aspect of the present invention, methods for depoting a lipophilic or other pharmaceutical agent in the adventitial tissue of a living vertebrate host, typically a human heart or other tissue, comprise positioning a microneedle through the wall of a coronary blood vessel and delivering an amount of the pharmaceutical agent into the perivascular space surrounding the blood vessel. The agent is delivered through an aperture in the microneedle directly into the perivascular space so that it distributes within the adventitial tissue surrounding the blood vessel. As described generally above, the interaction between the pharmaceutical agent and the lipid-containing adventitia provide for a depot or reservoir of the drug which is subsequently released into the blood vessel wall and other tissues in a controlled fashion over time. While the depoting pharmaceutical agent in the coronary adventitial tissue may find the greatest use, the depoting and release of drugs from other adventitial tissues located surrounding the peripheral vasculature will also find use in the treatment of peripheral vascular disease, as well as diseases of other organs and tissues.

Exemplary pharmaceutical agents for treating restenosis and hyperplasia include antiproliferative agents, immunosuppressive agents, anti-inflammatory agents, macrolide antibiotics, statins, anti-sense agents, metalloproteinase inhibitors, and cell cycle inhibitors and modulators. Agents for the treatment of arrhythmia include amiodarone, ibutilide, and mexiletine. Agents for the treatment of congestive heart failure include beta blockers, nitric oxide releasers, angiotensin converting enzyme inhibitors, and calcium channel antagonists. Agents for treatment of vulnerable (unstable) plaque include macrolide antibiotics, anti-inflammatory agents, statins, and thioglitazones. Agents for the treatment of vasospasm include cerapamil, and lapararin. A more complete listing of pharmaceutical agents suitable for treating coronary, vascular, and other diseased tissues and organs in accordance with the principles of the present invention is set forth in Table I below.

In a third aspect of the present invention, a method for delivering a pharmaceutical agent to a diseased treatment region in a coronary blood vessel comprises positioning a microneedle through the wall of a coronary artery at a delivery site spaced-apart from the diseased treatment region. The delivery site may be located within the same blood vessel as the diseased treatment region at a location which is longitudinally spaced-apart from said region, or may be located in a different blood vessel, including a different artery, or more usually, in a cognate coronary vein. In all cases, an amount of the pharmaceutical agent is delivered through an aperture in the microneedle into a perivascular space surrounding the delivery site so that the agent distributes into adventitial tissue surrounding the diseased treatment region to provide for the desired therapy. In some instances, the diseased treatment region may have been previously stented where the delivery site is spaced away from the stent, either longitudinally away from the stent in the same coronary artery or remote from the stent in another coronary artery or vein.

In still further aspects of the present invention, kits for delivering pharmaceutical agents to a patient suffering from or at risk of coronary artery or other vascular or non-vascular disease comprise a catheter and instructions for use of the catheter. The catheter has a microneedle which can be advanced from a blood vessel lumen through a wall of the blood vessel to position an aperture of the microneedle at a perivascular space surrounding the blood vessel. The instructions for use set forth any of the three exemplary treatment protocols described above.

The present invention still further comprises the use of a catheter having a microneedle in the manufacture of an apparatus for delivering pharmaceutical agents to a patient suffering from coronary artery disease. The pharmaceutical agent is delivered from a blood vessel lumen into a perivascular space surrounding the blood vessel so that the agent distributes circumferentially through the adventitial tissue surrounding the blood vessel. Usually, the agent will also distribute longitudinally along the blood vessel over a distance of at least 5 cm within a time of no greater than 5 minutes, usually within 1 minute or less. In some cases, the agent may further distribute into regions of the adventitia surrounding other blood vessels.

In another aspect of the present invention, methods and apparatus are provided for confirming that the aperture of the pharmaceutical agent injection needle is present beyond the external elastic lamina (EEL) before delivering pharmaceutical agent. As discussed above, it will often be desirable to place the delivery aperture of the pharmaceutical agent delivery needle just beyond the outside periphery or perimeter of the EEL prior to injection of the desired pharmaceutical agent. The difficulty with such positioning is that the thickness of the EEL can vary significantly, typically being from 0.1 mm to 5 mm thick, usually being less than 3 mm thick. The effective deployed needle length may not always be sufficient to assure that the delivery aperture is in the preferred 0 mm to 5 mm cylindrical envelope region outside of the EEL. Moreover, variations in thickness of plaque and other obstructive material which may be present on the interior of the blood vessel can also affect the ability of the needle to penetrate the vascular wall and position the delivery aperture at the requisite distance beyond the periphery of the EEL. Thus, in order to assure that the drug will enter this preferred cylindrical envelope surrounding the blood vessel, it is useful to confirm the position of the delivery aperture prior to delivery of the pharmaceutical agent.

Confirmation of the position of the pharmaceutical agent delivery aperture can be achieved in a variety of ways. Most simply, a bolus of radio opaque contrast agent or other visible media can be injected through the needle after initial positioning of the needle is achieved. By then observing the distribution of the media, usually fluoroscopically, the position of the aperture can be assessed. If the needle still lies within the EEL, the bolus will remain contained within the wall and will appear to have well defined edges and will usually taper longitudinally as the wall is dissected. If the aperture is properly positioned outside of the EEL, in contrast, the media will diffuse longitudinally along the vessel in the desired pattern. Finally, if the needle has extended beyond the preferred adventitial space and into muscle, the media will usually follow a non-homogenous diffusion pattern between the muscle fibers. Only when the desired pattern characteristic of adventitial delivery is confirmed will the pharmaceutical agent then be delivered.

In other cases, various sensors can be attached or otherwise coupled to the delivery needle, usually near the delivery aperture, in order to detect the position of the needle. Useful sensors include temperature sensors, pH sensors, electrical impedance sensors, and the like. It is also possible to measure back pressure on an injected fluid, either saline or other non-active agent or the pharmaceutical agent itself, in order to determine the needle position. Injection into the blood vessel wall will typically result in a greater back pressure than injection into the adventitial space. It will also be possible to monitor the insertion force of the needle, e.g., by providing a deflection gauge on a portion of the needle, or otherwise.

The present invention still further provides methods and systems for inhibiting inflammation in a patient's vasculature, said method comprising identifying a patient at risk of or suffering from vascular inflammation, positioning a catheter within a lumen of a blood vessel of the patient, advancing a needle radially outwardly from the catheter through the blood vessel wall and into adventitial tissue surrounding the blood vessel at a target location, and delivering (typically injecting) an anti-inflammatory agent into the adventitial and perivascular tissue in an amount sufficient to inhibit inflammation of the blood vessel. As used herein, inhibit shall mean to reduce or prevent inflammation in the patient's vasculature.

In specific aspects of the methods for inhibiting arterial and other vascular inflammation, the patient may be at risk of or suffering from peripheral artery disease, particularly in an artery selected from the group consisting of iliac arteries, femoral arteries, popliteal arteries, tibial arteries, and peroneal arteries. In other aspects, the patient may be at risk of or suffering from coronary artery disease. Exemplary anti-inflammatory agents include corticosteroids including mineralocorticoids and glucocorticoids, statins and non-steroidal anti-inflammatory drugs (NSAIDs), with dexamethasone being a preferred specific example. Vascular inflammation may be detected based a lack of a significant increase or a reduction, respectively, in biomarker levels in circulating blood such as high sensitivity C-reactive protein and monocyte chemotractive protein-1. Thus, these markers can serve as useful indicators of the ability of the present invention to reduce inflammation, where these markers can be detected in systemic circulating blood. These markers are typically increased by twofold or more upon injury of arterial tissues in the body, so the prevention, inhibition, or reduction of such rise is indicative of the ability to combat localized inflammation.

BRIEF DESCRIPTION OF THE DRAWINGS

FIGS. 6A and 6B illustrate the initial stage of the injection of a pharmaceutical agent into a perivascular space using the catheter of FIG. 3. FIG. 6A is a view taken across the blood vessel and FIG. 6B is a view taken along the longitudinal length of the blood vessel.

FIGS. 7A and 7B are similar to FIGS. 6A and 6B showing the extent of pharmaceutical agent distribution at a later time after injection.

FIGS. 8A and 8B are again similar to FIGS. 6A and 6B showing the extent of pharmaceutical agent distribution at a still later time following injection.

DETAILED DESCRIPTION OF THE INVENTION

The present invention will preferably utilize microfabricated catheters for intravascular injection. The following description provides two representative embodiments of catheters having microneedles suitable for the delivery of a pharmaceutical agent into a perivascular space or adventitial tissue. A more complete description of the catheters and methods for their fabrication is provided in U.S. Pat. No. 6,547,803 B2 the full disclosure of which has been incorporated herein by reference.

Figure 1:
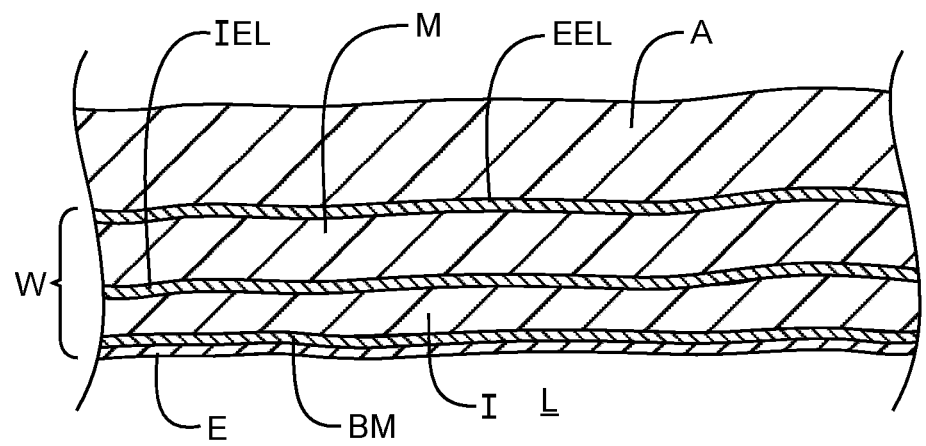
FIG. 1 is a schematic illustration of a coronary artery together with surrounding tissue illustrating the relationship between the perivascular space, the adventitia, and the blood vessel wall components.
Figure 1A:
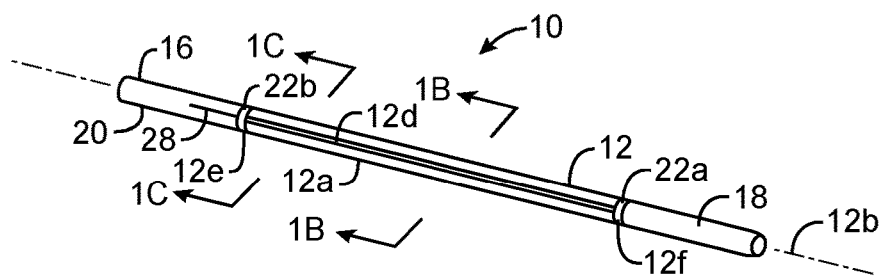
FIG. 1A is a schematic, perspective view of a microfabricated surgical device for interventional procedures in accordance with the methods and kits of the present invention in an unactuated condition.

The perivascular space is the potential space over the outer surface of a "vascular wall" of either an artery or vein. Referring to FIG. 1, a typical arterial wall is shown in cross-section where the endothelium E is the layer of the wall which is exposed to the blood vessel lumen L. Underlying the endothelium is the basement membrane BM which in turn is surrounded by the intima I. The intima, in turn, is surrounded by the internal elastic lamina IEL over which is located the media M. In turn, the media is covered by the external elastic lamina (EEL) which acts as the outer barrier separating the arterial wall, shown collectively as W, from the adventitial layer A. Usually, the perivascular space will be considered anything lying beyond the external elastic lamina EEL, including regions within the adventitia and beyond.

The microneedle is inserted, preferably in a substantially normal direction, into the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel terminated, and the actuator is operated to cause the microneedle to be thrust outwardly, substantially perpendicular to the central axis of a vessel, for instance, in which the catheter has been inserted.

Figure 1B:
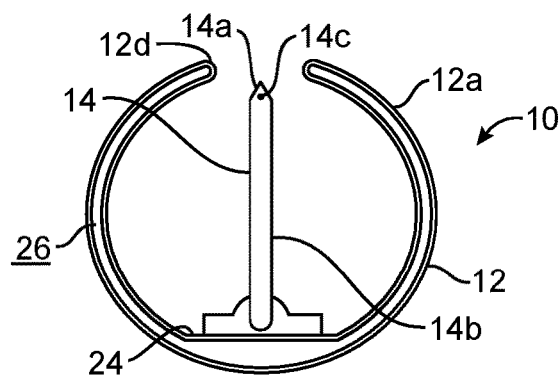
FIG. 1B is a schematic view along line 1B-1B of FIG. 1A.
Figure 1C:
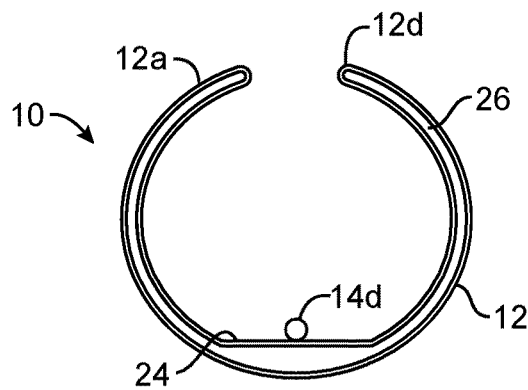
FIG. 1C is a schematic view along line 1C-1C of FIG. 1A.
Figure 2A:
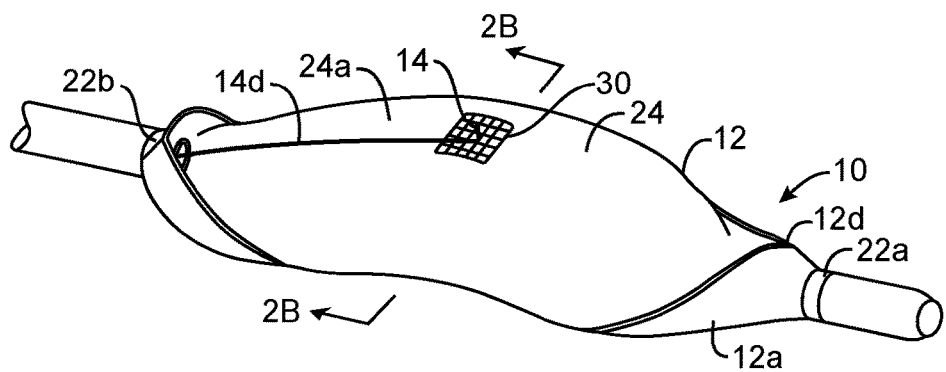
FIG. 2A is a schematic, perspective view of the microfabricated surgical device of FIG. 1A in an actuated condition.
Figure 2B:
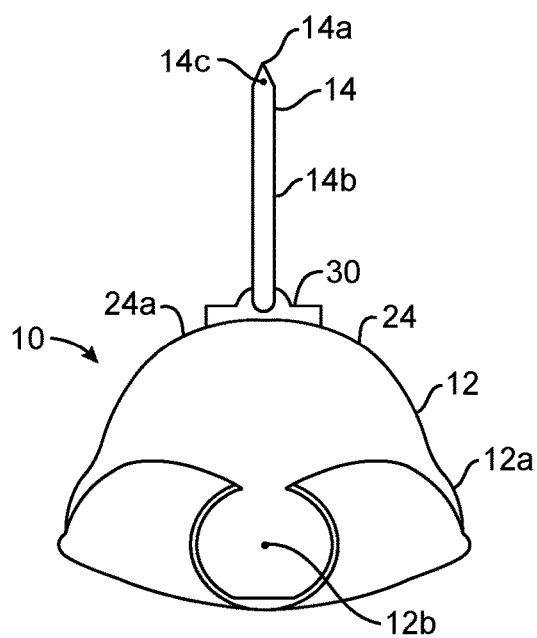
FIG. 2B is a schematic view along line 2B-2B of FIG. 2A.

As shown in FIGS. 1A-2B, a microfabricated intravascular catheter 10 includes an actuator 12 having an actuator body 12a and central longitudinal axis 12b. The actuator body more or less forms a C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a blood vessel by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (pm), substantially rigid material, such as parylene (types C, D or N), or a metal, for example, aluminum, stainless steel, gold, titanium or tungsten. The retaining rings form a rigid substantially "C"-shaped structure at each end of the actuator. The catheter may be joined to the retaining rings by, for example, a butt-weld, an ultra sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-rigid or rigid, expandable material, such as a polymer, for instance, parylene (types C, D or N), silicone, polyurethane or polyimide. The central section 24, upon actuation, is expandable somewhat like a balloon-device.

The central section is capable of withstanding pressures of up to about 100 atmospheres upon application of the activating fluid to the open area 26. The material from which the central section is made of is rigid or semi-rigid in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon© or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. The mesh-like structure (if included) may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a vessel or artery into which has been inserted, to allow direct puncture or breach of vascular walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of parylene, silicon or glass. Microneedles and methods of fabrication are described in U.S. patent publication 2002/0188310, entitled "Microfabricated Surgical Device", having common inventorship with but different assignment than the subject application, the entire disclosure of which is incorporated herein by reference.

Figure 3:
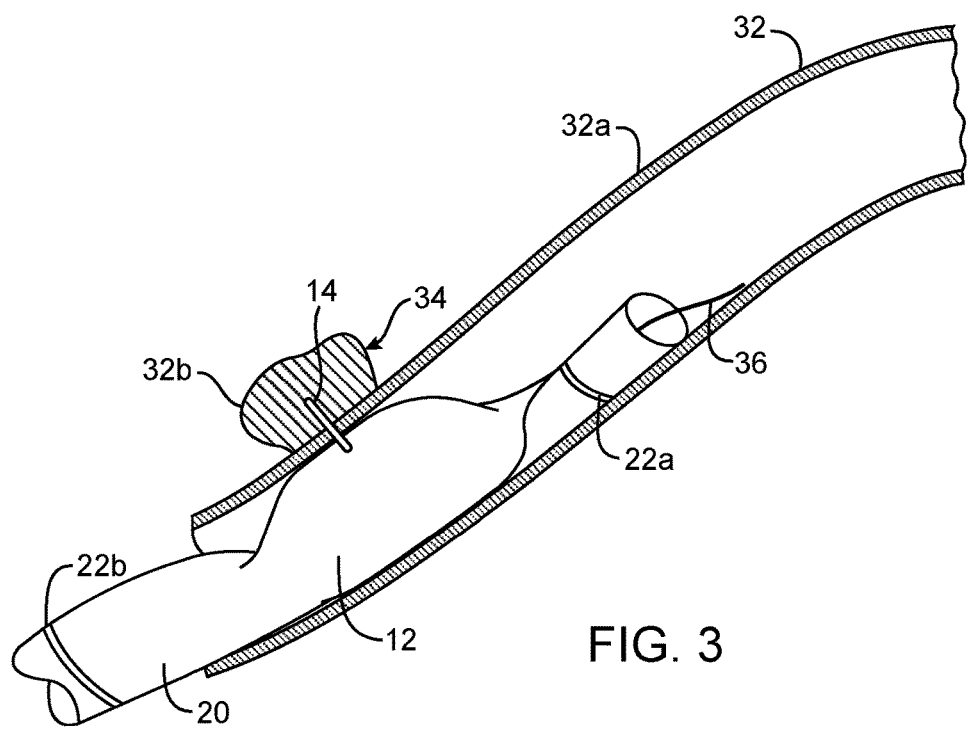
FIG. 3 is a schematic, perspective view of the microfabricated surgical device of the present invention inserted into a patient's vasculature.

The catheter 20, in use, is inserted through an artery or vein and moved within a patient's vasculature, for instance, an artery 32, until a specific, targeted region 34 is reaches (see FIG. 3). As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the vascular walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a vascular wall 32a. It may take only between approximately 100 milliseconds and two seconds for the microneedle to move from its furled state to its unfurled state.

The ends of the actuator at the retaining rings 22a and 22b remain rigidly fixed to the catheter 20. Thus, they do not deform during actuation. Since the actuator begins as a furled structure, its so-called pregnant shape exists as an unstable buckling mode. This instability, upon actuation, produces a large-scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 32b as well as vascular tissue. Additionally, since the actuator is "parked" or stopped prior to actuation, more precise placement and control over penetration of the vascular wall are obtained.

After actuation of the microneedle and delivery of the pharmaceutical to the target region via the microneedle, the activating fluid is exhausted from the open area 26 of the actuator, causing the expandable section 24 to return to its original, furled state. This also causes the microneedle to be withdrawn from the vascular wall. The microneedle, being withdrawn, is once again sheathed by the actuator.

By way of example, the microneedle may have an overall length of between about 200 and 3,000 microns (um). The interior cross-sectional dimension of the shaft 14b and supply tube 14d may be on the order of 20 to 250 um, while the tube's and shaft's exterior cross-sectional dimension may be between about 100 and 500 um. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 um. The diameter of the delivery tube for the activating fluid may be about 100 [tm to 1000 um. The catheter size may be between 1.5 and 15 French (Fr).

Figure 4:
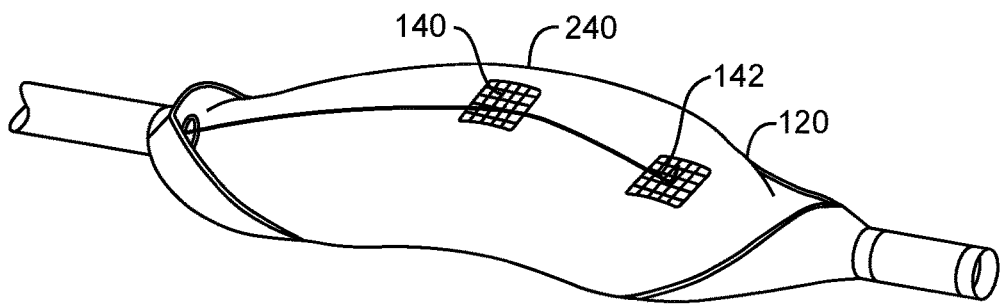
FIG. 4 is a schematic, perspective view of another embodiment of the device of the present invention.

Methods of the present invention may also utilize a multiple-buckling actuator with a single supply tube for the activating fluid. The multiple-buckling actuator includes multiple needles that can be inserted into or through a vessel wall for providing injection at different locations or times. For instance, as shown in FIG. 4, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time $t_1$, and pressure $p_1$, and the microneedle 142 moving at time $t_2$ and $p_2$, with $t_1$, and $p_1$, being less than $t_2$ and $p_2$, respectively.

This sort of staged buckling can also be provided with different pneumatic or hydraulic connections at different parts of the central section 240 in which each part includes an individual microneedle.

Figure 5:
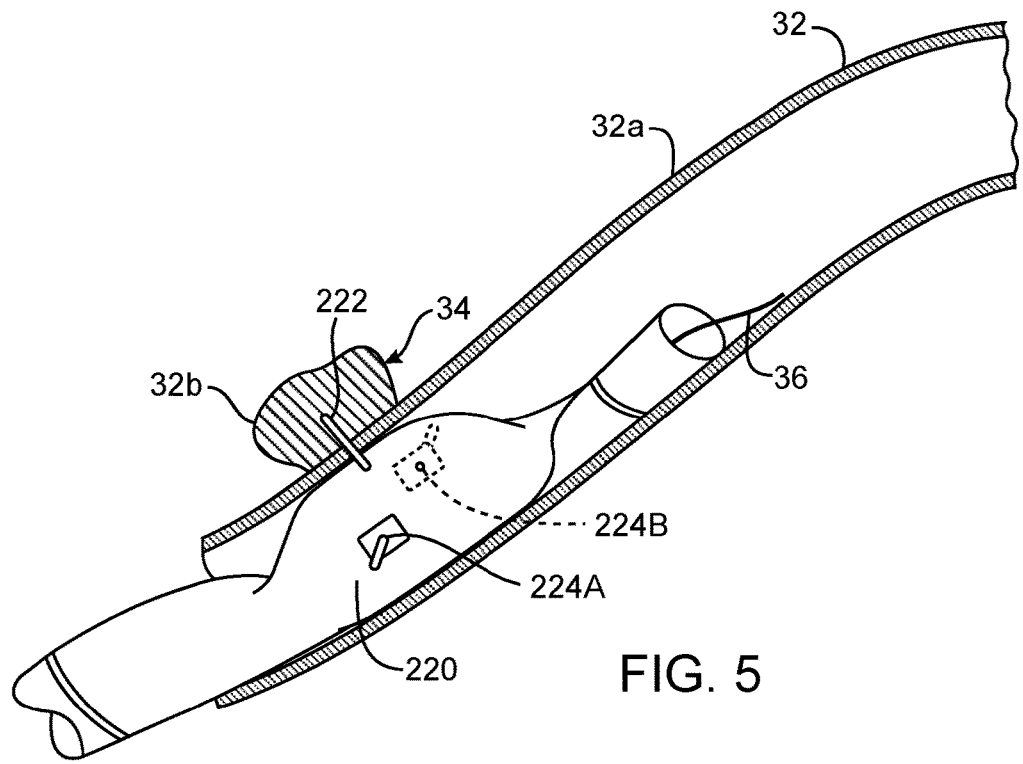
FIG. 5 is a schematic, perspective view of still another embodiment of the present invention, as inserted into a patient's vasculature.

Also, as shown in FIG. 5, an actuator 220 could be constructed such that its needles 222 and 224A move in different directions. As shown, upon actuation, the needles move at angle of approximately 90° to each other to puncture different parts of a vessel wall. A needle 224B (as shown in phantom) could alternatively be arranged to move at angle of about 180° to the needle 224A.

Referring now to FIGS. 6A/6B through FIGS. 8A/9B, use of the catheter 10 of FIGS. 1-3 for delivering a pharmaceutical agent according to the methods of the present invention will be described. The catheter 10 may be positioned so that the actuator 12 is positioned at a target site for injection within a blood vessel, as shown in FIGS. 6A/6B. The actuator penetrates the needle 14 through the wall W so that it extends past the external elastic lamina (EEL) into the perivascular space surrounding the EEL. Once in the perivascular space, the pharmaceutical agent may be injected, typically in a volume from 10 µl to 5000 µl, preferably from 100 µl to 1000 µl, and more preferably 250 µl to 500 µl, so that a plume P appears. Initially, the plume occupies a space immediately surrounding an aperture in the needle 14 and extending neither circumferentially nor longitudinally relative toward the external wall W of the blood vessel. After a short time, typically in the range from 1 to 10 minutes, the plume extends circumferentially around the external wall W of the blood vessel and over a short distance longitudinally, as shown in FIGS. 7A and 7B, respectively. After a still further time, typically in the range from 5 minutes to 24 hours, the plume will extend substantially completely circumferentially, as illustrated in FIG. 8A, and will begin to extend longitudinally over extended lengths, typically being at least about 2 cm, more usually being about 5 cm, and often being 10 cm or longer, as illustrated in FIG. 8B.

Figure 1D:
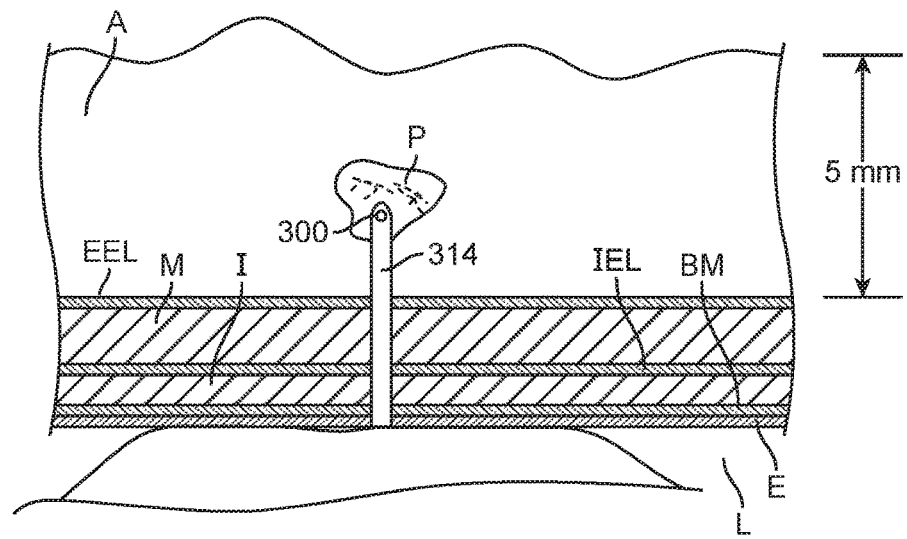
FIG. 1D is a schematic illustration of a microneedle having an aperture positioned at a preferred distance beyond the external elastic lamina (EEL) in accordance with the principles of the present invention.
Figure 1E:
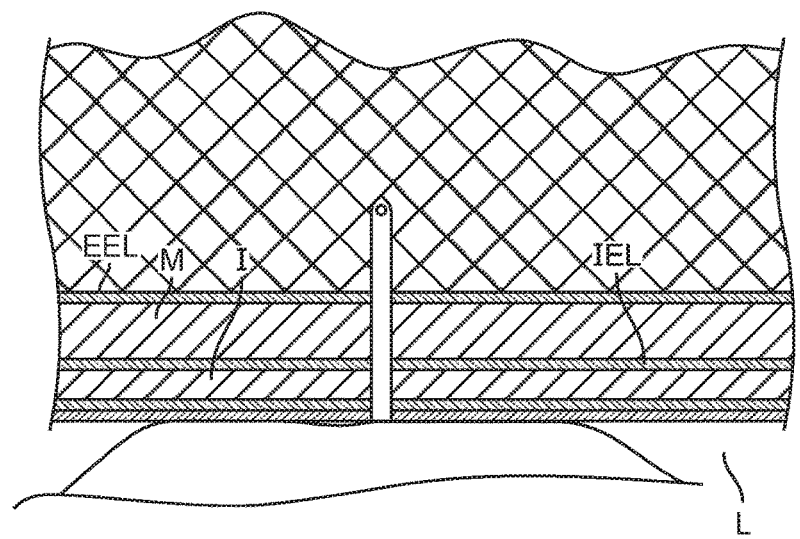
FIG. 1E illustrates the volumetric drug distribution achieved by the microneedle positioning of FIG. 1D.

Referring now to FIGS. 1D and 1E, a preferred protocol for positioning the aperture 300 of a microneedle 314 for volumetric delivery of a pharmaceutical agent in accordance with the principles of the present invention will be described. The aperture 300 is positioned from the lumen L of a blood vessel using any of the microneedle catheter systems described above. In particular, aperture 300 of the microneedle 314 is positioned beyond the external elastic lamina EEL by a distance of 5 mm or less, preferably 3 mm or less, and usually 0.5 mm or less, as described previously. To position the aperture within the requisite distance beyond the EEL, the needle must pass through the other layers of the blood vessel, as described above, in connection with FIG. 1A. Usually, these underlying layers will have a total thickness in the range from 0.1 mm to 5 mm, requiring that the needle extend from the blood vessel by a distance which is greater than the thickness of the wall. Once in position, the aperture 300 releases the pharmaceutical agent which then begins to form a plume P, as illustrated in FIG. 1D. By positioning beyond the blood vessel wall, but less than the 5 mm limit, it has been found that extensive volumetric distribution of the pharmaceutical agent can be achieved, as shown in FIG. 1E.

Because of variability in blood vessel wall thickness and obstructions which may limit the penetration depth of the needle being deployed, it will often be desirable to confirm that the pharmaceutical agent delivery aperture of the injection needle is present in the 5 mm annular envelope surrounding the delivery blood vessel prior to injection. Such confirmation can be achieved in a variety of ways.

Figure 3A:
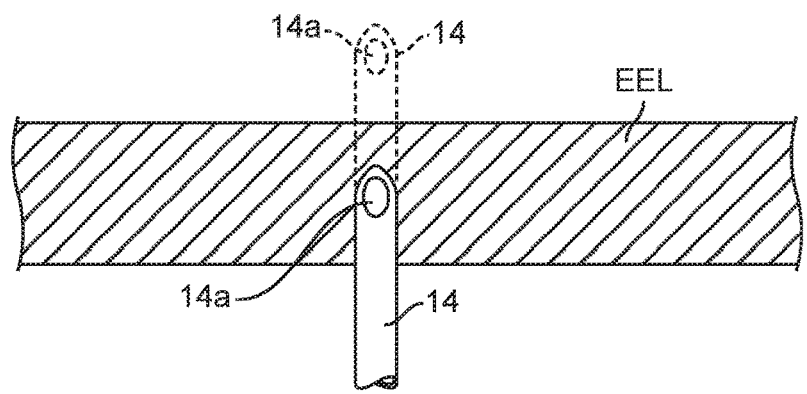
FIGS. 3A-3C illustrate the injection of a radio contrast media to help determine whether the pharmaceutical agent delivery aperture of an injection needle is properly placed within the preferred adventitial space surrounding a blood vessel.
Figure 3B:
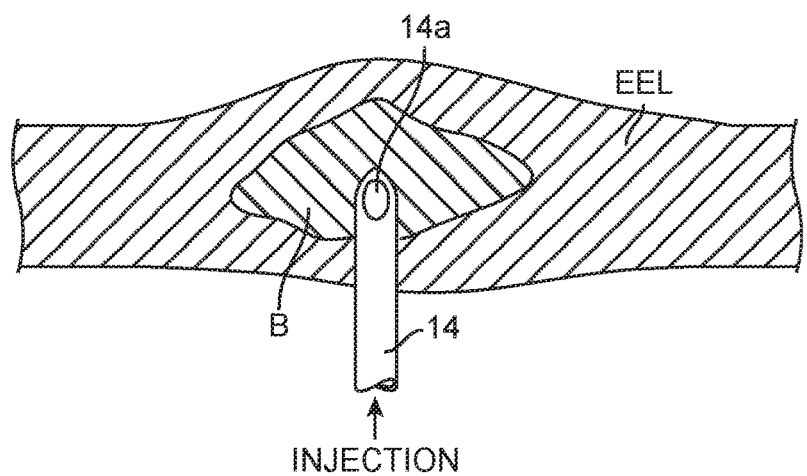
Figure 3C:
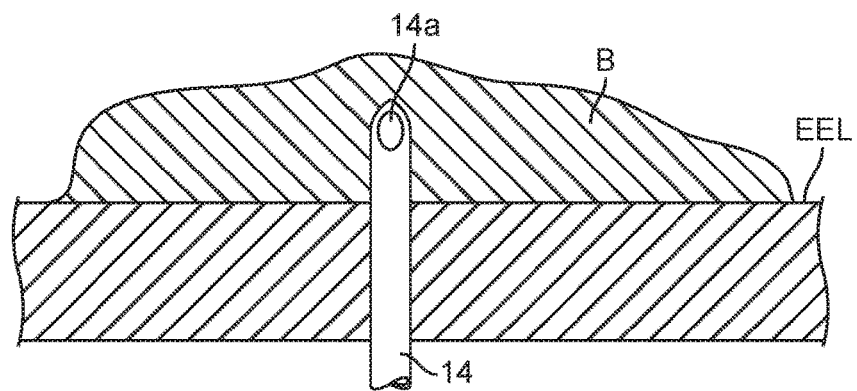
Figure 3D:
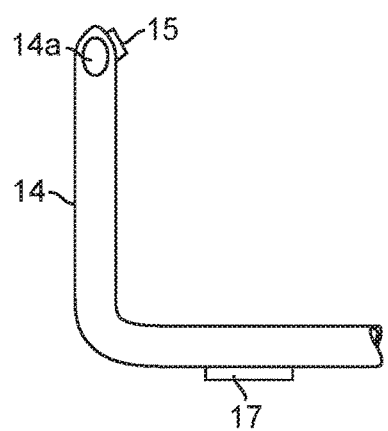
FIG. 3D illustrates the optional placement of sensors on a drug injection needle, which sensors can detect whether the needle has been advanced into the preferred adventitial space surrounding a blood vessel.

Referring to FIGS. 3A through 3C, the needle 14 of FIG. 3 can be positioned through the vascular wall so that it lies beyond the external elastic lamina (EEL), as shown in broken line in FIG. 3A. So long as the aperture 14a lies beyond the periphery of the EEL, and preferably a 5 mm annulus surrounding the vessel, successful delivery of the pharmaceutical agent can usually be achieved. To confirm that the aperture 14a lies within this target annual region, a bolus of contrast media can be injected prior to delivery of the pharmaceutical agent. If the aperture 14a has not penetrated through the EEL, as shown in FIG. 3B, then the bolus of contrast media will remain constrained within the wall of the vessel forming a well defined, generally tapered or ovoid mass B, as shown in FIG. 3B. In contrast, if the aperture 14a is positioned beyond the EEL, and within the desired annular region, the bolus B will spread longitudinally along the blood vessel wall in a very short period of time, indicating that the drug may be affectively delivered, as shown in FIG. 3C.

Other methods for confirming that the aperture 14a is properly positioned rely on presence of a sensor(s) 15 and/or located on the needle 14 usually near the aperture. Sensor 15 may be a solid state pressure sensor. If the pressure builds up during injection (either of an inactive agent or the pharmaceutical agent, it is likely that the aperture 14a still lies within the blood vessel wall. If the pressure is lower, the physician can assume that the needle has reached the adventitia. Sensor 15 may also be a temperature, such as a small thermistor or thermocouple, located at the tip of the needle adjacent over then the aperture 14a. The temperature within the blood vessel wall will be different than that outside of the EEL, making position function of temperature. The sensor may be a pH detector, where the tissue within the blood vessel wall and beyond the EEL have detectable differences in pH. Similarly, electrical impedance measurements characteristic of the tissues may be made with an impedance sensor 15. A deflection sensor 17, such as a flexible straining gauge, may be provided on a portion of the needle 14 which will deflect in response to insertion force. Insertion force through the blood vessel wall will be higher than that necessary to penetrate the tissue beyond the EEL. Thus, entry into the tissue beyond the EEL can be confirmed when the insertion force measured by the sensor 17 falls.

As just described, of course, the extent of migration of the pharmaceutical agent is not limited to the immediate region of the blood vessel through which the agent is been injected into the perivascular space. Instead, depending on the amounts injected and other conditions, the pharmaceutical agent may extend further into and through the myocardium other connective tissues so that it surrounds the extravascular spaces around other blood vessels, including both arteries and veins. As also described above, such broad myocardial, epicardial, or pericardial delivery can be particularly useful for treating non-localized cardiac conditions, such as conditions associated with congestive heart failure conditions associated with vulnerable or unstable plaque and conditions associated with cardiac arrhythmias. Delivery and diffusion of a pharmaceutical agent into a peripheral extravascular space can be particularly useful for treating diffuse vascular diseases.

The methods and kits described above may be used to deliver a wide variety of pharmaceutical agents intended for both local and non-local treatment of the heart and vasculature. Exemplary pharmaceutical agents include antineoplastic agents, antiproliferative agents, cytostatic agents, immunosuppressive agents, anti-inflammatory agents, macrolide antibiotics, antibiotics, antifungals, antivirals, antibodies, lipid lowering treatments, calcium channel blockers, ACE inhibitors, gene therapy agents, anti-sense drugs, double stranded short interfering RNA molecules, metalloproteinase inhibitors, growth factor inhibitors, cell cycle inhibitors, angiogenesis drugs, anti-angiogenesis drugs, and/or radiopaque contrast media for visualization of the injection under guided X-ray fluoroscopy. Each of these therapeutic agents has shown promise in the treatment of cardiovascular disease, restenosis, congestive heart failure, and/or vulnerable plaque lesions. Particular agents are set forth in Table I.

Distribution of fluorescent-labeled drug: Oregon Green® 488 paclitaxel (OGP) was injected into balloon-injured or normal porcine coronary arteries (15 arteries, 6 pigs) using a microneedle injection catheter having a needle with a diameter of 150 µm. Injections were made to depths in the range from 0.8 mm to 1.2 mm One artery was treated intraluminally with 5 mL OGP to determine background vascular uptake. Animals were sacrificed 0.5-23 hr post-procedure following IACUC-approved protocol. After sacrifice, the LAD, RCA and LCx were removed, cut into 4-5 mm sections, which were frozen and cryosectioned. The slides were counter-stained with 0.1% Evan's Blue in PBS (5 min 37 C) to quench autofluorescence, observed with a UV microscope, and scored 0-4+. Representative sections were photographed.

TABLE I

1. Antiproliferative agents, immunosuppressive agents, cytostatic, and anti-inflammatory agents, including but not limited to sulindac, tranilast, ABT-578, AVI-4126, sirolimus, tacrolimus, everolimus, cortisone, dexamethasone, cyclosporine, cytochalisin D, valsartin, methyl prednisolone, thioglitazones, acetyl salicylic acid, sarpognelate, and nitric oxide releasing agents, which interfere with the pathological proliverative response after coronary antioplasty to prevent intimal hyperplasia, smooth muscle cell activation and migration, and neointimal thickening.
2. Antineoplastic agents, including but not limited to paclitaxel, actinomycin D, and latrunculin A, which interfere with the pathological proliferative response after coronary angioplasty to prevent intimal hyperplasia, smooth muscle activation and migration and neointimal thickening.
3. Macrolide antibiotics, including but not limited to sirolimus, tacrolimus, everolimus, azinthromycin, clarithromycin, and erythromycin, which inhibit or kill microorganiss that may contribute to the inflammatory process that triggers or exacerbates restenosis and vulnerable plaque. In addition many macrolide antibiotics, including but not limited to sirolimus and tacrolimus, have immunosuppressive effects that can prevent intimal hyperplasia, neointimal proliferation, and plaque rupture. Other antibiotics, including but not limited to sirolumus, tacrolimus, everolimus, azithromycin, clarithromycin, doxycycline, and erothromycin, inhibit or kill microorganisms that may contribute to the inflammatory process that triggers or exacerbates restenosis and vulnerable plaque.
4. Antivirals, including but not limited to acyclovir, ganciclovir, fancyclovir and valacyclovir, inhibit or kill viruses that may contribute to the inflammatory process that triggers or exacerbates restenosis and vulnerable plaque.
5. Antibodies which inhibit or kill microorganisms that may contribute to the inflammatory process that triggers or exacerbates restenosis and vulnerable plaque or to inhibit specific growth factors or cell regulators.
6. Lipid-lowering treatments, including but not limited to statins, such as trichostatin A, which modify plaques, reducing inflammation and stabilizing vulnerable plaques.
7. Gene therapy agents which achieve overexpression of genes that may ameliorate the process of vascular occlusive disease or the blockade of the expression of the genes that are critical to the pathogenesis of vascular occlusive disease.
8. Anti-sense agents, including but not limited to AVI-4126, achieve blockade of genes and mRNA, including but not limited to c-myc, c-myb, PCNA, cdc2, cdk2, or cdk9s, through the use of short chains of nucleic acids known as antisense oligodeoxynucleotides.
9. Metalloproteinase inhibitors, including but not limited to batimastat, inhibit constrictive vessel remodeling.
10. Cell cycle inhibitors and modulators and growth factor inhibitors and modulators, including but not limited to cytokine receptor inhibitors, such as interleukin 10 or propagermanium, and modulators of VEGF, IGF, and tubulin, inhibit or modulate entry of vascular smooth muscle cells into the cell cycle, cell migration, expression chemoattractants and adhesion molecules, extracellular matrix formation, and other factors that trigger neointimal hyperplasia.
11. Angiogenesis genes or agents which increase microvasculature of the pericardium, vaso vasorum, and adventitia to increase blood flow.
12. Anti-angiogenesis genes or agents inhibit factors that are associated with microvascularization of atherosclerotic plaque and which directly or indirectly also induce smooth muscle cell proliferation.
13. Antithrombotics including but not limited to IIb/IIIa inhibitors, Abciximab, heparin, clopidigrel, and warfarin.

The following Experiments are offered by way of illustrations, not by way of limitation.

Experimental

Studies were performed to show visual and quantitative evidence of deposition of agents in the adventitia and distribution of the deposited agents from that site.

Acutely harvested tissue (<2 hr post-procedure) showed 4+ staining of the adventitia when OGP was delivered with the microneedle catheter through the vessel wall. With increasing time after delivery, drug penetrated into the media and extended longitudinally 13-24 mm (mean, 15 mm) from the injection site. At 23 hr, staining was observed throughout the circumference of the artery, with longitudinal extension of 23-32 mm (mean, 27.5 mm). OGP delivered into the lumen without needle deployment resulted in staining on the luminal surface only.

Distribution of silver nitrate: Two injections of 0.5 mL 5% Silver Nitrate were made into each iliac artery of a rabbit. The animal was sacrificed according to approved protocol following the last injection. The arteries were removed and placed in 10% formalin without perfusion. 2 mm segments were embedded in paraffin, sectioned, and hematoxylin-eosin stained.

Staining showed delivery outside the external elastic lamina of the vessels and diffusion around the circumference.

Distribution of a lipophilic compound (tacrolimus): Eight swine underwent angiography. Twenty-two coronary arteries (2.25-2.75 mm) received 125 micrograms tacrolimus in two 500 micrograms injections approximately 1 cm apart. The two remaining arteries served as untreated controls. An untreated heart was used as a negative control. At 48 hours arteries were dissected from the musculature and perivascular fat, cut into 5 mm sections and analyzed by Liquid Chromatography/Mass Spectrometry against tacrolimus calibration standards containing homogenized untreated porcine heart tissue.

Figure 9:
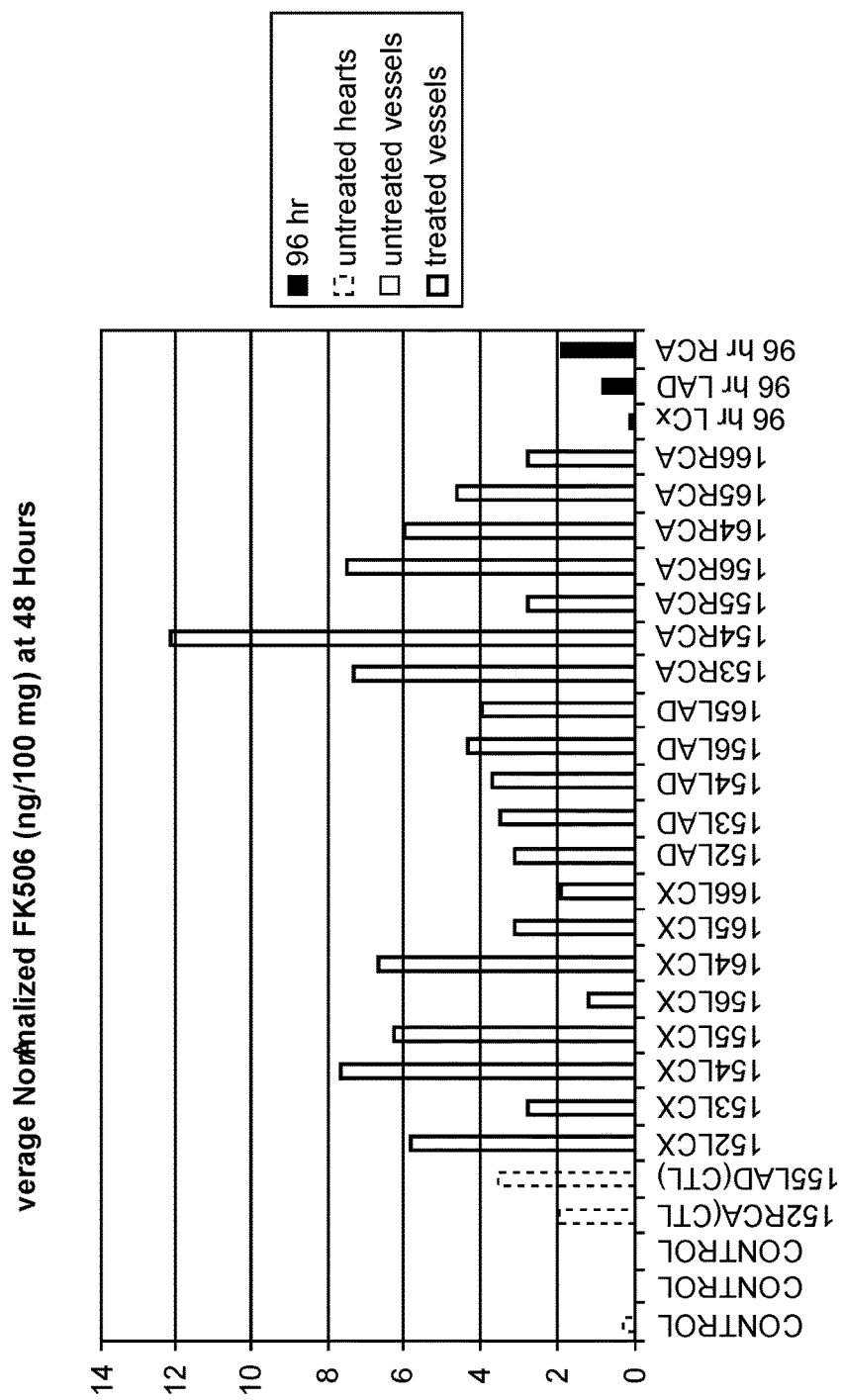
FIGS. 9 and 10 illustrate data described in the Experimental section herein.
Figure 10:
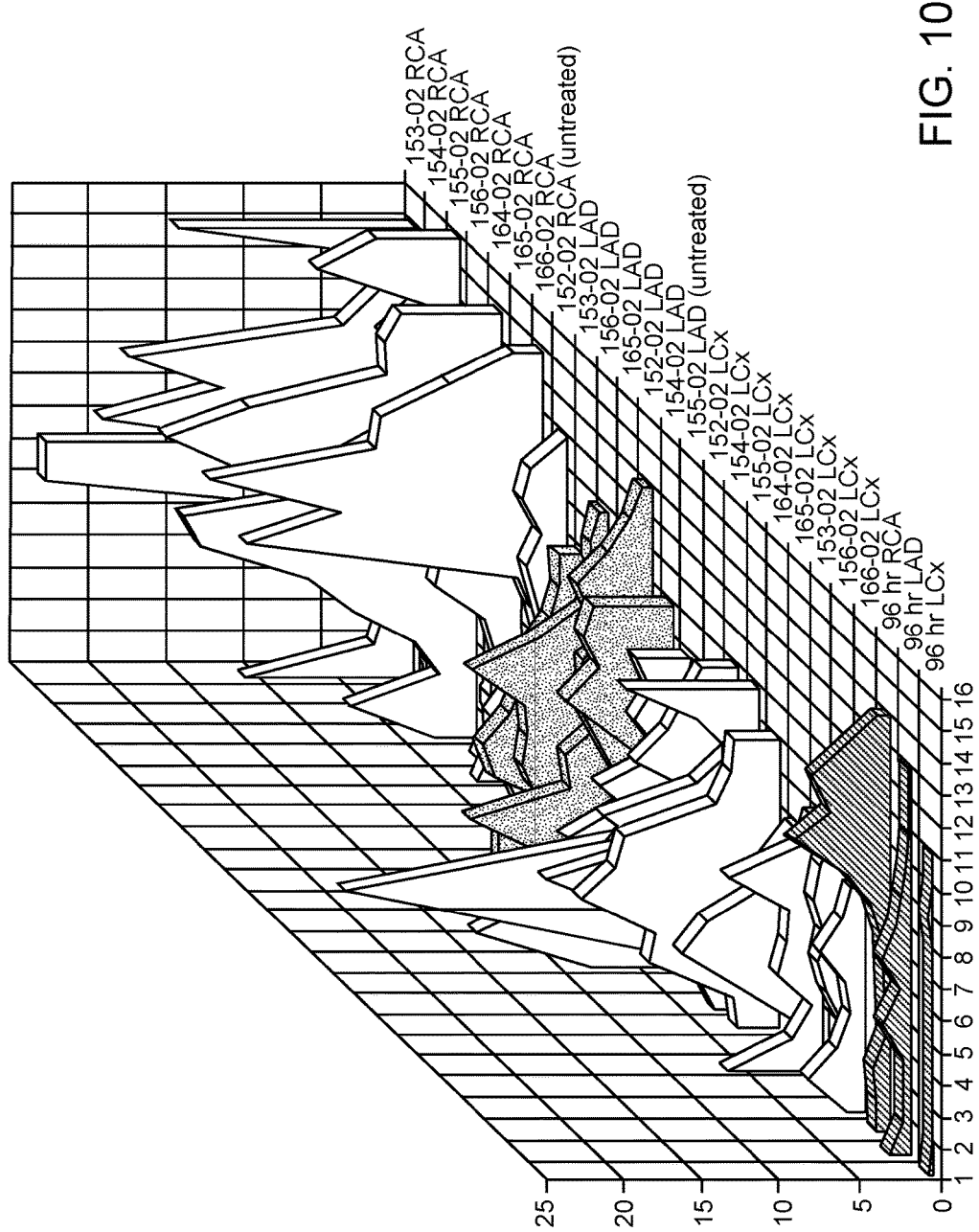

In 8/8 subjects, periadventitial delivery of tacrolimus resulted in distribution to the entire coronary tree with higher concentrations at injection sites. Drug was detected in 285/293 segments, including side branches and uninjected arteries. The mean levels of tacrolimus were 5.5 ng/100 mg tissue (SD=2.5, N=15) in the confirmed injected arteries, 2.7 ng/100 mg tissue (SD=1.1, N=2) in uninjected arteries of treated hearts, and 0.08 ng/100 mg tissue (SD=0.14, N=3) in uninjected arteries of the untreated heart. Mean concentration within 1 cm of known injection sites was 6.4 ng/100 mg tissue (SD=3.7, N=13) versus 2.6 ng/100 mg tissue (SD=1.5, N=13) in the remaining segments ($p<0.001$). Data are provided in FIGS. 9 and 10.

The microsyringe delivered agent to the adventitia, demonstrated by circumferential and longitudinal arterial distribution of fluorescent-labeled paclitaxel and silver nitrate. The paclitaxel studies showed that the distribution increased over time. Quantitative measurement of tacrolimus showed distribution of drug the full length of the artery, which was detectable 48 hours after injection.

Figure 11A:
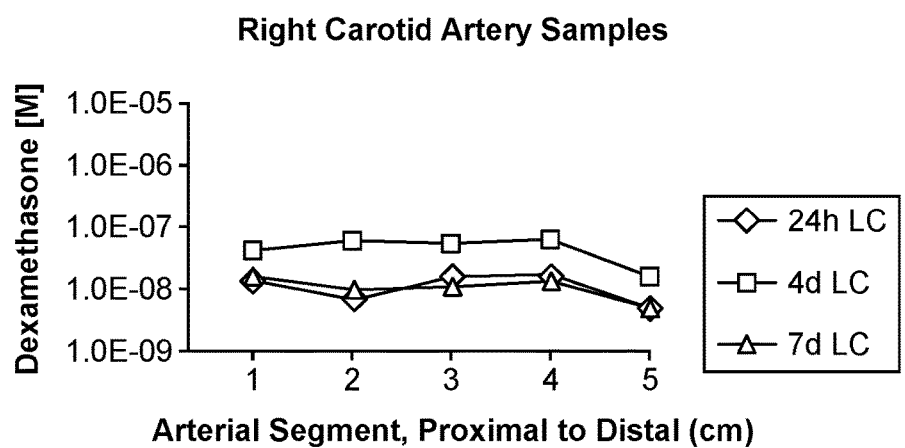
FIGS. 11A and 11B show dexamethasone levels measured in pig carotid arteries 1, 4, and 7 days after confirmed delivery of 1 mg dexamethasone sodium phosphate in 3 ml volume to the carotid artery adventitia with the Bullfrog Micro-Infusion Catheter. Delivery was made in segment 3 in each case. Each line represents a single artery.
Figure 11B:
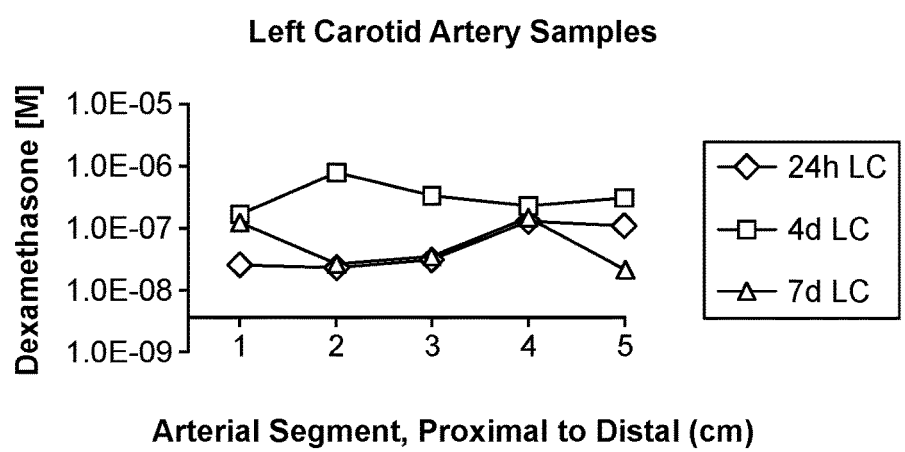

In further studies, dexamethasone uptake and persistence in tissues has been demonstrated in a study using a Bullfrog® Micro-Infusion Catheter for delivery of dexamethasone to the adventitial tissue of porcine carotid arteries. In this study, sustained levels in the range of 10 to 100 nM were seen 1, 4, and 7 days after infusion of 1 mg. The results are shown in FIGS. 11A and 11B.

Additionally, a study was designed to compare a high dose of dexamethasone (10 mg equivalent dose of dexamethasone phosphate) delivered in 3 ml volume to the perivascular tissue of porcine AV grafts (6 mm ringed PTFE) implanted between femoral artery and femoral vein pairs, bilaterally. Fourteen days after graft implantation, percutaneous transluminal angioplasty (PTA) was performed (7 mm balloon, 16 atmosphere inflation pressure) at two sites per graft: across the graft-vein anastomosis (GVA) and in the proximal vein (PV). Perivascular infusion of either dexamethasone (6 grafts) or placebo (2 grafts) was administered following the PTA procedure. Infusions of 3 ml were always consistent between the 2 grafts in each animal. Animals were euthanized 14 days after the treatment procedure and the graft-vein anastomosis and proximal vein were analyzed by histopathology and histomorphometry to determine adverse effects from the high dose of dexamethasone. The study was not intended to identify differences in stenosis but rather was aimed at determining dexamethasone local toxicity.

The histopathology findings of the study indicated that femoral GVA treated with angioplasty and perivascular, high-dose dexamethasone, via the Bullfrog® Micro-Infusion Catheter, exhibited no negative differences compared to GVA treated with angioplasty and perivascular placebo.

Twenty patients have been enrolled into a U.S. single-center, open-label, pilot clinical trial of dexamethasone delivery to femoral and popliteal adventitia. Patients with TASC II A, B, and C disease of the superficial femoral and/or popliteal arteries were eligible for this study. Following successful intervention with balloon angioplasty, provisional atherectomy in 4/20 patients and a provisional stenting determination in 6/20 patients, an adventitial micro-infusion catheter, (Bullfrog®, Mercator MedSystems, San Leandro, Calif.), was advanced over a 0.014" wire to the treated segment. Its micro-needle (0.9 mm long×140 m diameter) was deployed into the adventitia to deliver dexamethasone (DEX, 4 mg/ml) mixed with iodixanol contrast agent (80:20 ratio), providing fluoroscopic visualization.

Lesion lengths ranged from 2.3 to 25.2 cm (8.9±5.3 cm, N=20). Lesions were in the distal SFA or popliteal artery 80% of the time and in proximal or mid SFA 20% of the time. Dosage: 12.1±6.1 mg (range: 3.2 to 24 mg) of dexamethasone was delivered, with 1.6±1.1 mg dexamethasone per cm lesion and 4.2±1.4 mg (range: 2.4 to 8.0 mg) of dexamethasone per infusion. Procedural safety was seen in 100% of patients, with a lack of drug-related or device-related serious adverse events or major adverse limb events (amputation or major vascular re-intervention in the index limb) within 30 days of the procedure. Only one drug or device-related adverse event was reported within 30 days of the procedure: acute hyperglycemia in one patient, controlled by post-procedural insulin. Patients have been followed for 381±181 days. The twenty patients had returned for a 6 month follow up prior to the time of this analysis. Of those twenty patients, two had experienced a target lesion restenosis, as defined by a peak systolic velocity ratio (PSVlesion/PSVreference)>2.4 or occlusion noted by ultrasound. Three out of the twenty patients have experienced a target extremity stenosis that was not within the treated segment. In fifteen patients that (a) were followed up at 6 months with an ankle-brachial index examination, and (b) did not have any target vessel restenosis, ankle-brachial index has improved from 0.67±0.17 pre-op to 0.88±0.18 at 6 months (P<0.003). All patients but the one with target lesion restenosis had improved Rutherford classification scores at 6 months as compared to pre-op baseline scores. Out of twelve patients reaching their one-year follow up, ten did not have index lesion restenosis, with PSVR of 1.1±0.6 (N=8), and with ABI measurements of 1.04±0.21 (N=10, P<0.0001 vs baseline). Furthermore, the anticipated rise of high sensitivity C-Reactive Protein (hsCRP) as noted by Schillinger, M., et al., [Balloon angioplasty and stent implantation induce a vascular inflammatory reaction. J Endovasc Ther, 2002. 9(1): p. 59-66.] appears to be dampened in patients treated with perivascular dexamethasone, indicating that this novel route of administration is capable of not only building up therapeutic levels of the drug, but that the drug is retained by tissue long enough to have a desired anti-inflammatory effect.

Dexamethasone is a well-known anti-inflammatory agent with no observable adverse effect when compared to placebo in the adventitia of human or porcine AV graft, post-angioplasty.

A survey of published literature, along with internal research, indicates that:

1. The adventitia is the locus of inflammatory cell recruitment and agglomeration in response to vessel injury, thus it is the most appropriate target to prevent resultant hyperplastic reactions,
2. Dexamethasone inhibits the expression of inflammatory proteins that are expressed in the adventitia,
3. Dexamethasone is retained in the blood vessel wall and adventitia at therapeutic concentrations for at least 7 days after adventitial infusion of dosages that are lower than those clinically approved for soft-tissue infiltration, and
4. Dexamethasone has been used in millions of direct injections for anti-inflammatory therapy with an excellent safety record.

We believe that the combination of (a) rapid cellular uptake, (b) known inhibitory effects on specific cell types and cytokines present within the injured lesion of arterial neointimal hyperplasia, (c) its anti-inflammatory properties, and (d) its minimal toxicity and extensive clinical use to date; makes dexamethasone an ideal agent for adventitial infusion to prevent restenosis due to vascular injury from angioplasty, atherectomy or stenting.

In the in-vivo experience, the Bullfrog® Micro-Infusion Catheter has safely and successfully delivered dexamethasone sodium phosphate or placebo material marked with dilute contrast medium (a) to native porcine peripheral arteries and (b) to the porcine model and human AV graft, post-angioplasty. Infusions of contrast solutions are visible under fluoroscopy, providing positive feedback to physicians of infusate location and spread. The infusion of agents into diseased human peripheral arteries has been confirmed in more than 25 patients. The procedure has been safe and the device has effectively delivered therapeutic agents to the vasculature.

A first-in-human study to test the safety and feasibility of dexamethasone administration through a microinfusion catheter according to the present invention (Bullfrog®, Mercator MedSystems, Inc, San Leandro, Calif.) was performed. Dexamethasone was injected into the superficial femoral and popliteal artery (http://www.clinicaltrials.gov). Unique identifier: NCT 01507558). The study design was a prospective, single-center, investigator-initiated study that enrolled consecutive patients who met eligibility requirements from the San Francisco Veteran Affairs Medical Center. This study was approved by the Committee for Human Research and the University of California Clinical and Translational Science Institute. Safety data and outcomes were monitored by a Data Safety and Monitoring Committee that convened on a quarterly basis or as needed.

The primary inclusion criteria were patients suffering from moderate to severe disabling claudication, ischemic rest pain, or minor tissue loss secondary to atherosclerotic lower extremity occlusive disease with TransAtlantic Inter-Society Consensus II A-D lesions of the superficial femoral artery (SFA) or popliteal arteries. The minimal reference vessel lumen diameter was required to be 3 to 6 mm, and the patient was required to have at least one infrapopliteal runoff vessel. Exclusion criteria included serum creatinine ≥2.5 mg/dL, prior revascularization of the target limb, known allergy to contrast agents or dexamethasone, estimated life expectancy less than 1 year, or other concurrent illness in which the investigators thought would limit the patient's ability to follow the schedule of assessments.

Figure 12:
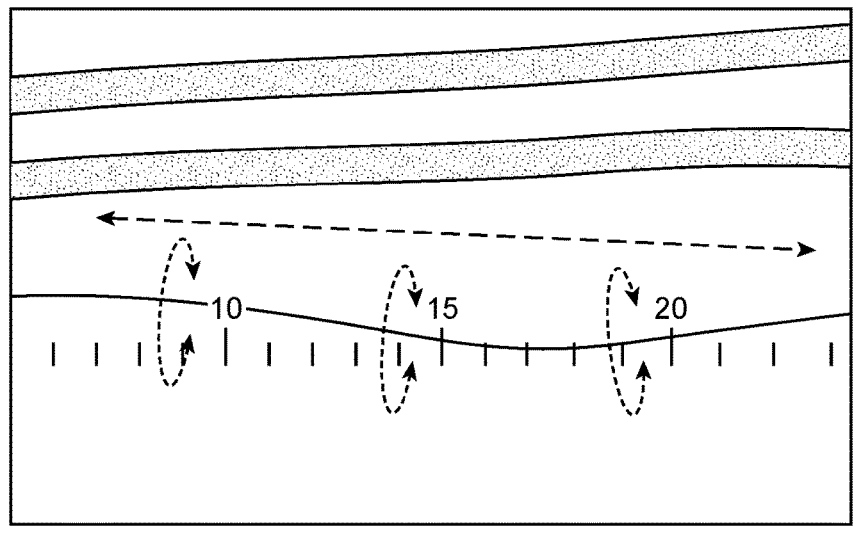
FIG. 12 is a fluoroscopic image of endovascular treatment with adjunctive dexamethasone as described in the Experimental section. The patient a 49-year-old man with severe disabling claudication and a 16-cm superficial femoral artery (SFA) occlusion. Following securing access across the lesion with a glide wire, the lesion was treated with balloon angioplasty. Following successful angioplasty, four 1.0-mL injections were performed along the length of the lesion (only three shown). In the left panel, there is a discreet contrast blush seen at each injection site. Note that the contrast appears circumferentially at each injection site. Three minutes later, the drug-contrast admixture can be seen to have diffused longitudinally to fully cover the treated segment. The patient is now 2 years from his index procedure and remains patent and complains of only mild claudication with heavy exertion. He has an ankle-brachial index (ABI) of 1.09 and a peak systolic velocity ratio of less than 2.5.
Figure 12:
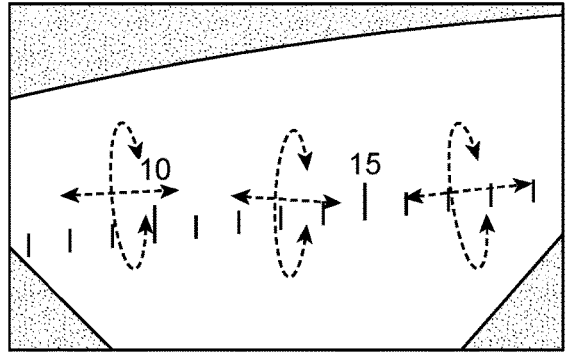

The Bullfrog® Micro-Infusion is a rapid-exchange, wire-guided catheter with a balloon-sheathed 0.9-mm-long, 35-gauge (140 μm diameter) needle that delivers infusions to adventitial and perivascular tissues. It is Food and Drug Administration 510(k)-cleared for use in coronary and peripheral arteries. It is advanced through a 6 F sheath over a 0.014-inch wire and can treat vessels from 3 to 6 mm in diameter. Three radio-opaque markers on the catheter allow for proper orientation of the needle. Using standard angioplasty inflation equipment, the balloon was inflated exposing the needle. When the balloon contacted the arterial wall opposite the needle tip, contact pressure forced the needle through the vessel wall and into the adventitia and perivascular tissues. The contact pressure of the balloon against the artery wall is limited to 2 atmospheres by a pressure release valve, which prevents damage to the artery wall. A mixture of infusate and contrast (4:1) was then delivered under fluoroscopic guidance into the adventitia. A test injection of 0.1 mL was made to confirm proper adventitial placement of the microinfusion needle tip. If resistance is met, or the test injection enters the blood stream, the balloon was deflated and the injection is attempted in another location by moving the catheter a few millimeters proximally or distally or rotating the catheter a few degrees. Once adventitia placement was confirmed, the remainder of the infusate was delivered at a rate of 1 mL/min. When the infusion was complete, the balloon was deflated, sheathing the needle, and allowing the catheter to be withdrawn. FIG. 12. Injections were administered approximately every 3 cm along the length of the treated arterial segment. Because the drug:contrast admixture can be visualized on both sides of the arterial wall, only one fluoroscopic view was necessary to confirm circumferential arterial coverage in the majority of cases.

Patients not taking aspirin or clopidogrel before study enrollment received 325 mg of aspirin 12 hours prior the procedure. Postprocedure, patients were prescribed 81 mg/d of aspirin to be taken indefinitely and 75 mg/d of clopidogrel daily for 12 weeks. Vascular access was accomplished by either the contralateral or ipsilateral (anterograde) approach. Patients received a bolus of 5000 IU of heparin after insertion of the sheath in the common femoral artery, and their activated clotting time was kept above 250 seconds with additional heparin as needed. In the case of chronic total occlusions, all lesions were crossed subintimally with a glide wire and glide catheter (Terumo, Somerset, N.J.). After securing access across the lesion with a guidewire, the target lesion was treated according to physician preference. All patients were treated with balloon angioplasty. If a flow-limiting dissection or residual stenosis was determined to require a stent, the protocol specified for treatment with dexamethasone prior to stent placement. In all cases, the microinfusion catheter was advanced to the treatment site following angioplasty to deliver dexamethasone into the arterial adventitia.

Following the procedure, all patients were admitted for a 23-hour observation period for access site, adverse event, and revascularization monitoring. Prior to discharge, ankle-brachial indexes (ABIs) and arterial duplex ultrasound studies were performed in the vascular laboratory. Blood was drawn at baseline and at 24 hours following the procedure to assess the inflammatory response.

The dosage utilized in this protocol was an off-the-shelf concentration of dexamethasone sodium phosphate for injection USP, 4 mg/mL, which is approved for reducing soft tissue inflammation. Specifically, dexamethasone is indicated for soft tissue injection of 0.4 to 6 mg to treat acute exacerbations in a variety of inflammatory conditions. Based on these similar uses of the drug to treat localized inflammation, it was postulated that a similar dose (2-6 mg) should be used to treat each 3 cm of lesion (0.7-2 mg/cm), allowing for multiple infusions in the case of long lesions. The 3-cm benchmark was chosen based on typical longitudinal perivascular diffusion patterns in preclinical ex vivo cadaveric femoral artery studies (unpublished data). The dexamethasone sodium phosphate for injection USP, which contains 4.0 mg dexamethasone phosphate per milliliter, was mixed 80%:20% with an iso-osmolar iodinated contrast medium (iodixanol 320 mg I/mL; GE HealthCare, Cork, Ireland) resulting in a final concentration of 3.2 mg dexamethasone phosphate and 60 to 74 mg of iodine in each milliliter of solution. The final dosing target was, therefore, determined to be approximately 0.5 mL of the diluted drug per centimeter of lesion or 1.6 mg/cm.

Figure 13:
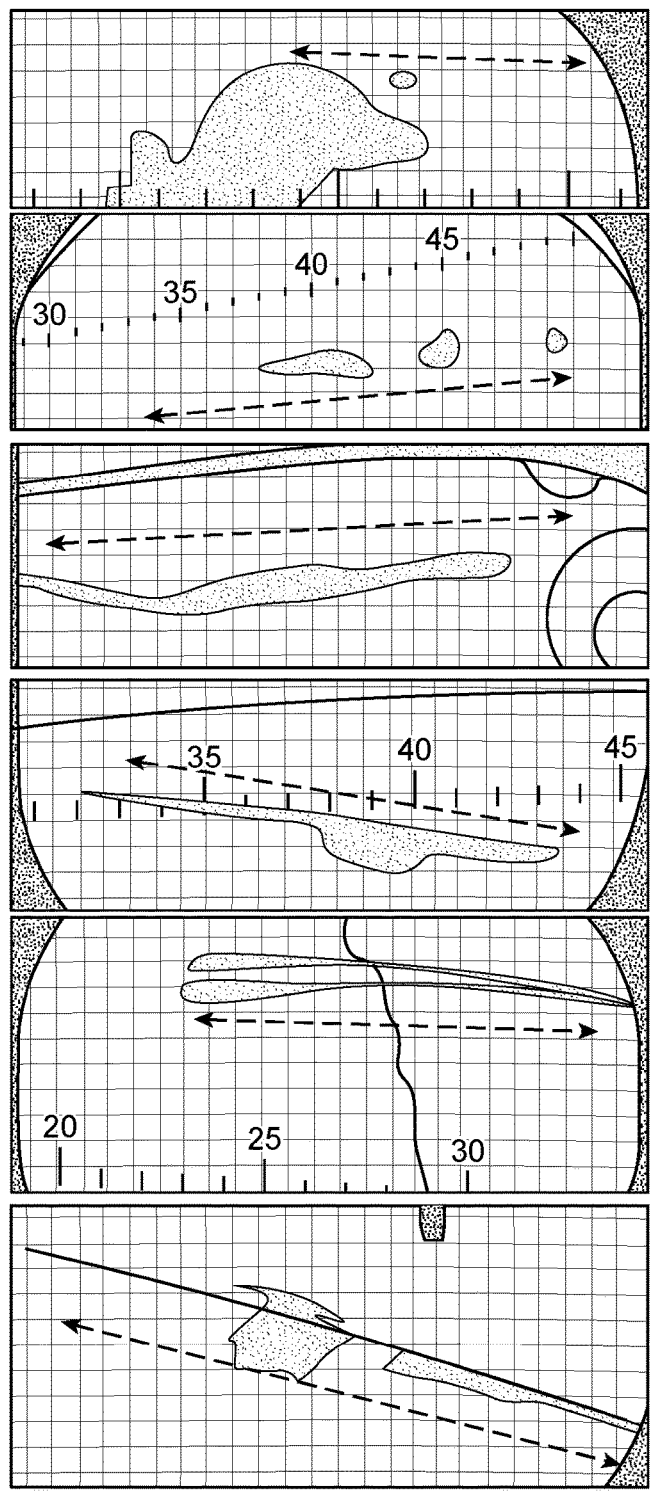
FIG. 13 shows examples of typical dexamethasone-contrast diffusion patterns in treated patients treated.

The coinfusion of contrast medium with the drug allowed the X-ray fluoroscopic visualization required to positively assess infusion success (FIGS. 12 and 13). All infusions were graded based on the circumferential and longitudinal distribution of the drug/contrast infusate and the coverage of the target lesion. For example, an infusion that was completely circumferential and extended 3 cm in either direction from the point of injection would be considered a diffusion grade A. If infusions were only partially circumferential or partially longitudinal, then a grade of B was given.

Medical history was obtained before the procedure, including concomitant medication use, Rutherford clinical category, resting ABI, and laboratory results for baseline C-reactive protein (CRP), serum creatinine, and lipids. Adverse event evaluation was performed at the end of the index procedure and at each follow-up visit. Patients were then reassessed with vascular history and physical examination, ABIs, and duplex arterial ultrasound examinations at 1, 3, and 6 months. The primary safety end point was freedom from death, vessel perforation, dissection, thrombosis, or pseudoaneurysm formation within 30 days following the procedure. The primary feasibility end point was procedural success for adventitial infusion of dexamethasone and contrast at the target lesion as determined by the relationship of the fluoroscopic blush to the treatment segment. While not powered for an efficacy signal, the primary efficacy end point was a primary patency rate defined as freedom from the combined end points of target lesion revascularization, occlusion, or >50% restenosis in the treated lesion. Duplex ultrasonography was performed to assess restenosis and >50% restenosis was defined by a peak systolic velocity ratio >2.5. Rates of target lesion revascularization, death, and amputation end points were also analyzed. Secondary end points were change in Rutherford classification and ABI from baseline to 6 months.

Inflammation as detected by plasma CRP has been linked to restenosis following peripheral intervention. As one of our intended goals was to reduce inflammation following vascular intervention, serum CRP was measured at baseline and 24 hours following the procedure.

This study was not powered for clinical outcomes. Normally distributed continuous variables were expressed as mean and standard deviation and were evaluated with the Student t-test or one-way analysis of variance where appropriate. Proportions were evaluated by the $\chi^2$ test. Rutherford classification and categorical variables were assessed by the Kruskal-Wallis test. Safety parameters were collected and assessed qualitatively or summarized quantitatively by descriptive statistics. Statistical significance was set at the two-tailed 0.05 level.

Demographic and clinical characteristics are presented in Table II. In brief, 20 male patients were enrolled in this study with 35% African American and 50% Caucasian. The mean age of this cohort was 66.5±9.8 years, and 55% had diabetes mellitus. Eighty percent of the patients had claudication, the majority had a preoperative Rutherford score of 3 (65%), and the mean preoperative ABI index was 0.68±0.15. Lesion characteristics treated in this study are presented in Table III. The mean lesion length was 8.9±5.3 cm (2.3-25.2 cm), and 50% of treated lesions were chronic total occlusions. Eighty percent of lesions were located in the distal SFA and/or popliteal artery. The mean reference vessel diameter was 4.8±0.1 mm. Six patients (30%) required the placement of a self-expanding stent because of residual stenosis or flow-limiting dissection following balloon angioplasty. The lesion characteristics of the patients who received stents including percentage occlusions or lesion length were not different than those who were not stented.

TABLE II

Baseline patient demographics and clinical characteristics

| | |
|---|---|
| Age, years | 66 ± 10 |
| Male sex | 20 (100) |
| Race | |
| Caucasian | 10 (50) |
| African American | 7 (35) |
| Hispanic | 2 (10) |
| Asian | 1 (5) |
| Diabetes mellitus | 11 (55) |
| Coronary artery disease | 11 (55) |
| Hypertension | 19 (95) |
| Hyperlipidemia | 20 (100) |
| Body mass index, kg/m$^2$ | 27.4 ± 4.5 |
| Creatinine, mg/dL | 1.0 ± .34 |
| CRP, mg/dL | 6.9 ± 8.5 |
| Total cholesterol, mg/dL | 149.1 ± 37.5 |
| Rutherford classification | 3 = Moderate claudication |
| | 13 = Severe claudication |
| | 3 = Ischemic rest pain |
| | 1 = Minor tissue loss |
| Index limb ABI | .68 ± .15 |
| Age, years | 66 ± 10 |
| Male sex | 20 (100) |
| Race | |
| Caucasian | 10 (50) |
| African American | 7 (35) |
| Hispanic | 2 (10) |
| Asian | 1 (5) |
| Diabetes mellitus | 11 (55) |
| Coronary artery disease | 11 (55) |
| Hypertension | 19 (95) |
| Hyperlipidemia | 20 (100) |
| Body mass index, kg/m$^2$ | 27.4 ± 4.5 |
| Creatinine, mg/dL | 1.0 ± .34 |
| CRP, mg/dL | 6.9 ± 8.5 |
| Total cholesterol, mg/dL | 149.1 ± 37.5 |
| Rutherford classification | 3 = Moderate claudication |
| | 13 = Severe claudication |
| | 3 = Ischemic rest pain |
| | 1 = Minor tissue loss |
| Index limb ABI | .68 ± .15 |

TABLE III

Lesion Characteristics

| | |
|---|---|
| SFA location | Proximal SFA, 2 (10) |
| | Mid-SFA, 2 (10) |
| | Distal SFA, 8 (40) |
| | Popliteal, 8 (40) |
| Lesion length,[a] cm | 8.9 ± 5.3 |
| Reference vessel diameter, mm | 4.8 ± .1 |
| Diameter stenosis (%) | 78.5 |
| Occlusion | 10 (50) |
| % Occlusion | 88 ± 12 |

TABLE III-continued

Lesion Characteristics

| | |
|---|---|
| TASC II classification | A = 5 |
| | B = 11 |
| | C = 2 |
| | D = 2 |
| Revascularization method | PTA in 20 patients (100%) |
| | +atherectomy in three patients (15%) |
| | +provisional stent in six patients (30%) |

PTA, Percutaneous transluminal angioplasty; SFA, superficial femoral artery; TASC, TransAtlantic Inter-Society Consensus.
Continuous data are presented as mean ± standard deviation and categoric data as number (%).
$^a$Normal-to-normal lesion length as assessed by principal investigator.

In all cases, dexamethasone was able to be delivered to the adventitia of the target lesion. The mean number of injections required per lesion was 3.0±1.3 cm, minimum one and maximum six injections. Each injection was graded on an ordinal descriptive scale. In 19 out of 20 subjects, there was complete circumferential coverage of the lesion with the infusate as assessed immediately after the infusion (grade=A). In one patient, there was only partial coverage noted by contrast distribution (grade=B). The mean volume injected was 3.8±1.9 mL, which contained a mean of 12.1±6.1 mg of dexamethasone sodium phosphate and 0.80±0.4 mL of contrast. This equated to a mean of 1.6±1.1 mg of dexamethasone sodium phosphate per centimeter of lesion length. The minimal dose was 3.2 mg, and the maximal dose a patient received was 24 mg of dexamethasone sodium phosphate. Accordingly, there was a positive. Technical success markers are shown in FIG. 13.

The post-intervention immune response following femoropopliteal intervention has been shown to be independently associated with subsequent restenosis. The preoperative CRP for subjects in this study was 6.9±8.5 indicating severe baseline inflammation, which increased to 14.0±23.1 mg/L (103% increase) at 24 hours following the procedure indicating that there was an inflammatory response following peripheral intervention. However, this increase did not reach statistical significance (P=0.14).

Figure 14:
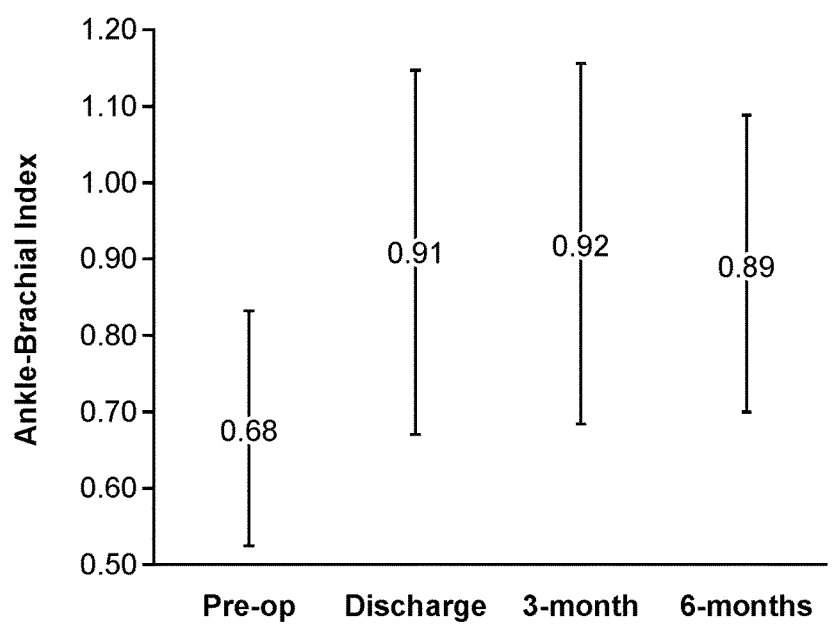
FIG. 14 shows that the mean ankle-brachial index (ABI) was significantly improved from baseline across all time points post procedure.

Two patients in this study reached the primary end point of loss of primary patency by duplex ultrasound-determined binary restenosis by 6 months. The first, a 77-year-old man who had an 11.9 cm chronic total occlusion involving the distal SFA extending into the popliteal artery treated with balloon angioplasty and a 7- by 100-mm Everflex stent (Covidien, Plymouth Minn.) was found to have reoccluded his lesion at 172 days following the procedure. The second patient is a 63-year-old man that had a 10-cm popliteal artery occlusion, which was treated by angioplasty and was found to have reoccluded 182 days following his procedure. The mean preoperative Rutherford score decreased from 3.1±0.71 (median, 3.0) preoperatively to 0.5±0.70 (median, 0) at 6 months; P<0.00001. Over this same time interval, the preoperative index leg ABI increased from 0.68±0.15 (range, 0.22-0.89) to 0.89±0.19 (range, 0.49-1.2; P=0.0003; FIG. 14.

Figure 15:
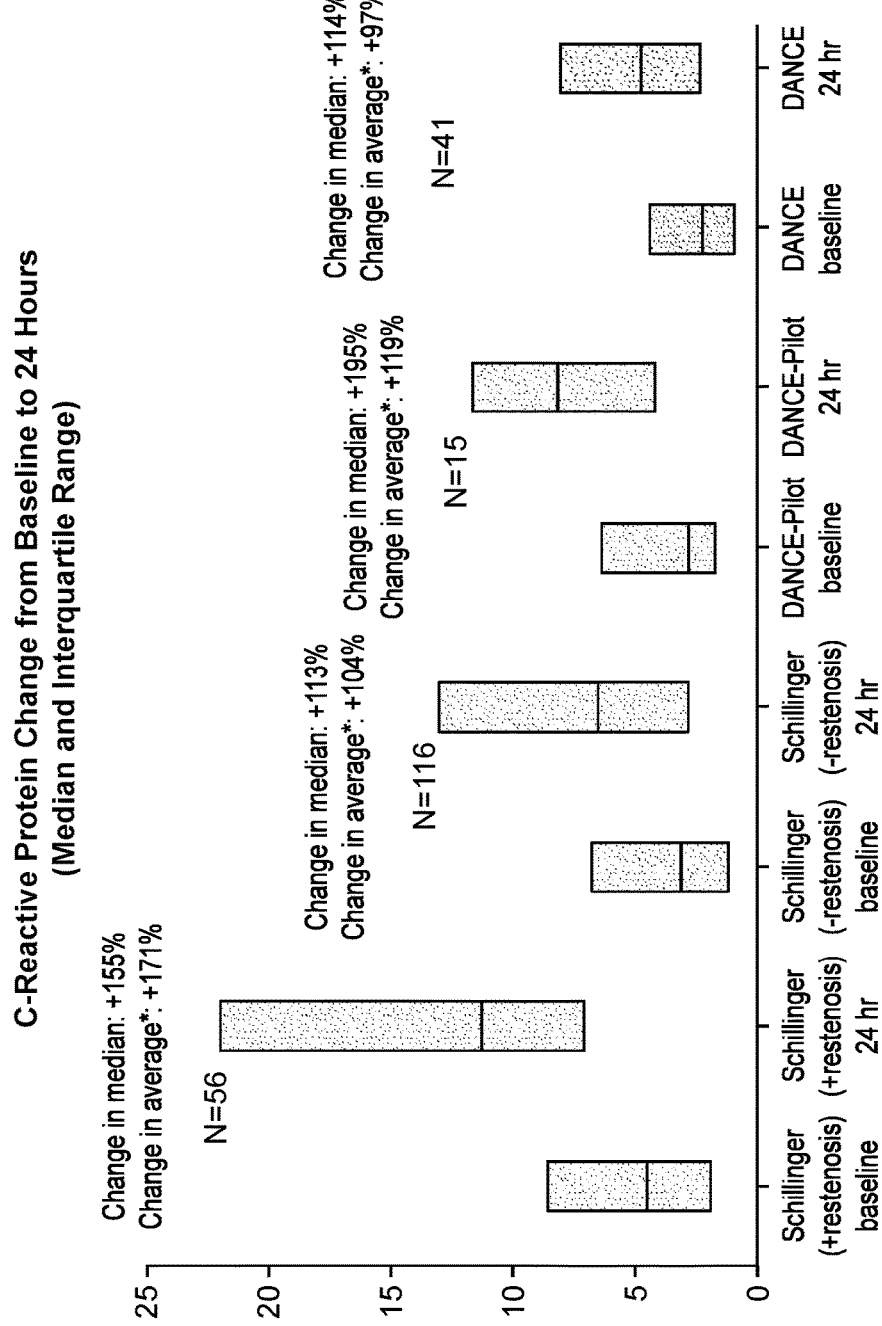
FIG. 15 shows the median and interquartile range of high sensitivity C-reactive protein (hsCRP) detected in circulating serum of patients from Schillinger 2002 published research with restenosis by 6 months post-procedure, patients from Schillinger 2002 without restenosis by 6 months post-procedure, patients from the DANCE-Pilot study, and patients from the DANCE Trial. These data indicate that delivery of dexamethasone in conjunction with revascularization therapy is able to reduce inflammation and thus improve upon patency results.

An additional study has enrolled 140 patients in the United States, meeting similar enrollment criteria as those in the 20-patient study described above. In these patients, approximately one-third of them have had blood draws right before a revascularization procedure of their superficial femoral or popliteal artery, and then again at 24±4 hours after their revascularization procedure. Arterial lesions in this study were at least 70% occlusive prior to revascularization and up to 15 cm in length. Revascularization therapy was performed with angioplasty, atherectomy, provisional stenting, or a combination thereof. Right after revascularization therapy, dexamethasone was delivered into the adventitia and perivascular tissues around the vessel at an approximate concentration of 1.6 mg per longitudinal centimeter of lesion treated. The Schillinger 2002 published research would indicate the likelihood for a substantial rise in the hsCRP after revascularization therapy, and that this rise is linked to the rate of restenosis at 6 months following the revascularization procedure. The data from Schillinger 2002 and the 20-patient study described above (the DANCE-Pilot, in which 15 patients had baseline and 24 hour hsCRP levels examined) are plotted in FIG. 15, along with 41 patients from the larger 139 patient group (the DANCE Trial). The notable change from expected levels of hsCRP found in this 41 patient group indicates that dexamethasone, when delivered and confirmed to be delivered into the perivascular tissue and adventitia around revascularized arteries, is capable of reducing the inflammatory spike that leads to further recruitment of inflammatory and remodeling cells, proliferation of the cells and inflammatory signal locally around the artery, and eventual migration of cells and fibrosis that leads to renarrowing of the blood vessel, or restenosis. See FIG. 15.

Figure 16:
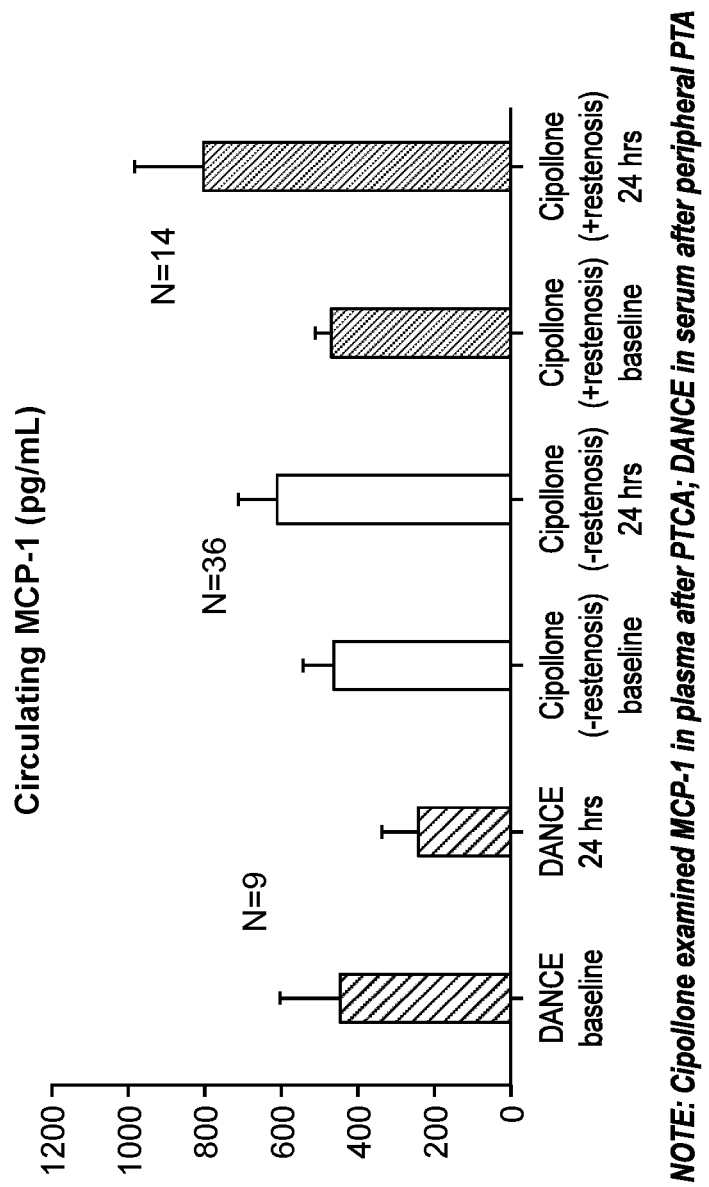
FIG. 16 shows the average and standard deviation of circulating monocyte chemotractive protein-1 (MCP-1) in patients from the DANCE trial as well as patients from Cipollone 2001 published research, displaying a typical rise in MCP-1 after angioplasty in coronary arteries, but a drop in MCP-1 when peripheral artery revascularization was paired with adventitial and perivascular delivery of dexamethasone with a dosage of approximately 1.6 mg per longitudinal centimeter of lesion treated (DANCE).

Additional data coming out of the interim analysis of the DANCE study includes the first 9 patients to have MCP-1 analyzed from their circulating blood at baseline and at 24 hours. This testing indicates that rather than the expected rise in MCP-1, the use of dexamethasone to reduce inflammation, in fact, causes a marked drop in MCP-1 on average. The control of these inflammatory factors steers the body's healing processes away from switching into an aggressive fibrosis-driven and scar tissue generating process, but keeps them in a pro-healing mode, leading to less scarring and less restenosis of the arteries over time. See FIG. 16.

A number of embodiments of the invention have been described. Nevertheless, it will be understood that various modifications may be made without departing from the spirit and scope of the invention as claimed hereinafter.

What is claimed is:

1. A method for inhibiting inflammation in a patient's vasculature, said method comprising:
    positioning a catheter within a lumen of a blood vessel of the patient, the blood vessel having had a revascularization procedure performed thereon;
    advancing a needle radially outwardly from the catheter through a wall of the blood vessel and into an adventitial tissue surrounding the blood vessel; and
    delivering an anti-inflammatory agent into the adventitial tissue and a perivascular tissue through the needle advanced into the adventitial tissue in an amount sufficient to inhibit inflammation of the blood vessel after the revascularization procedure, wherein the anti-inflammatory agent consists essentially of dexamethasone or dexamethasone phosphate,
    wherein the inhibition or a reduction of inflammation is characterized by a detectable lack of a significant increase or a detectable reduction, respectively, in monocyte chemotractive protein-1 (MCP-1) levels in circulating blood.

2. The method of claim 1, wherein the patient is at risk of or suffering from peripheral artery disease.

3. The method of claim 2, wherein the blood vessel is an artery selected from the group consisting of iliac arteries, femoral arteries, and popliteal arteries.

4. The method of claim 1, wherein the anti-inflammatory agent is delivered at a dosage of 3.2 mg to 24 mg.

5. The method of claim 1, wherein the anti-inflammatory agent is delivered at a dosage of 0.5 to 2.7 mg per cm of lesion.

6. The method of claim 1, wherein the anti-inflammatory agent is delivered at a dosage of 2.4 mg to 8.0 mg per infusion.

7. The method of claim 1, wherein the delivered anti-inflammatory agent distributes completely circumferentially through the adventitial tissue surrounding the blood vessel at a delivery site.

8. The method of claim 1, wherein the anti-inflammatory agent is delivered right after revascularization.

9. The method of claim 1, further comprising delivering a contrast agent for visualization through the needle advanced into the adventitial tissue.

10. The method of claim 9, wherein the anti-inflammatory agent is delivered with the contrast agent at a primary therapeutic agent to contrast agent ratio of 4:1.

11. The method of claim 1, wherein the anti-inflammatory agent is incorporated into a lipophilic carrier or adjuvant.

12. The method of claim 1, wherein the anti-inflammatory agent is delivered with saline.

13. The method of claim 1, wherein the anti-inflammatory agent is incorporated into liposomes.

14. The method of claim 1, wherein the anti-inflammatory agent is delivered with an erodable polymer.

15. The method of claim 1, wherein the anti-inflammatory agent is delivered with a solubilizer.

16. The method of claim 1, wherein the anti-inflammatory agent is provided as microparticles or nanoparticles.

17. The method of claim 1, wherein the method further comprises withdrawing the needle from the adventitial tissue and withdrawing the catheter out of the blood vessel of the patient after delivering the anti-inflammatory agent.

18. A method for inhibiting inflammation in a patient's vasculature, said method comprising:
    positioning a catheter within a lumen of a blood vessel of the patient, the blood vessel having had a revascularization procedure performed thereon;
    advancing a needle radially outwardly from the catheter through a wall of the blood vessel and into an adventitial tissue surrounding the blood vessel; and
    delivering an anti-inflammatory agent into the adventitial tissue and a perivascular tissue through the advanced needle in an amount sufficient to inhibit inflammation of the blood vessel after the revascularization procedure, wherein the anti-inflammatory agent comprises dexamethasone or dexamethasone phosphate, and wherein the dexamethasone or the dexamethasone phosphate is delivered into the adventitial tissue and the perivascular tissue at a dosage of 0.5 to 2.7 mg per cm of lesion,
    wherein the inhibition or a reduction of inflammation is characterized by a detectable lack of a significant increase or a detectable reduction, respectively, in monocyte chemotractive protein-1 (MCP-1) levels in circulating blood.

19. The method of claim 18, wherein the patient is at risk of or suffering from peripheral artery disease.

20. The method of claim 19, wherein the blood vessel is an artery selected from the group consisting of iliac arteries, femoral arteries, and popliteal arteries.

21. The method of claim 18, wherein the anti-inflammatory agent is delivered at a dosage of 3.2 mg to 24 mg.

22. The method of claim 18, wherein the anti-inflammatory agent is delivered at a dosage of 2.4 mg to 8.0 mg per infusion.

23. The method of claim 18, wherein the delivered anti-inflammatory agent distributes completely circumferentially through the adventitial tissue surrounding the blood vessel at a delivery site.

24. The method of claim 21, wherein the anti-inflammatory agent is delivered right after revascularization.

25. The method of claim 18, further comprising delivering a contrast agent for visualization through the needle advanced into the adventitial tissue.

26. The method of claim 25, wherein the anti-inflammatory agent is delivered with the contrast agent at a primary therapeutic agent to contrast ratio of 4:1.

27. The method of claim 18, wherein the anti-inflammatory agent is incorporated into a lipophilic carrier or adjuvant.

28. The method of claim 18, wherein the anti-inflammatory agent is delivered with saline.

29. The method of claim 18, wherein the anti-inflammatory agent is incorporated into liposomes.

30. The method of claim 18, wherein the anti-inflammatory agent is delivered with an erodable polymer.

31. The method of claim 18, wherein the anti-inflammatory agent is delivered with a solubilizer.

32. The method of claim 18, wherein the anti-inflammatory agent is provided as microparticles or nanoparticles.

33. The method of claim 18, wherein the method further comprises withdrawing the needle from the adventitial tissue and withdrawing the catheter out of the blood vessel of patient after delivering the anti-inflammatory agent.

* * * * *